US010466478B2

(12) United States Patent
Klug et al.

(10) Patent No.: US 10,466,478 B2
(45) Date of Patent: Nov. 5, 2019

(54) EYE IMAGING WITH AN OFF-AXIS IMAGER

(71) Applicant: Magic Leap, Inc., Dania Beach, FL (US)

(72) Inventors: Michael Anthony Klug, Austin, TX (US); Adrian Kaehler, Los Angeles, CA (US)

(73) Assignee: Magic Leap, Inc., Plantation, FL (US)

( * ) Notice: Subject to any disclaimer, the term of this patent is extended or adjusted under 35 U.S.C. 154(b) by 199 days.

(21) Appl. No.: 15/271,802

(22) Filed: Sep. 21, 2016

(65) Prior Publication Data
US 2017/0082858 A1    Mar. 23, 2017

Related U.S. Application Data

(60) Provisional application No. 62/222,671, filed on Sep. 23, 2015.

(51) Int. Cl.
*G02B 27/01* (2006.01)
*A61B 3/10* (2006.01)
*G02C 11/00* (2006.01)
*A61B 3/113* (2006.01)
*A61B 3/12* (2006.01)
(Continued)

(52) U.S. Cl.
CPC ............ *G02B 27/0172* (2013.01); *A61B 3/10* (2013.01); *A61B 3/113* (2013.01); *A61B 3/12* (2013.01); *A61B 3/14* (2013.01); *A61B 5/1122* (2013.01); *A61B 5/163* (2017.08); *A61B 5/742* (2013.01); *G02B 27/0093* (2013.01);
(Continued)

(58) Field of Classification Search
CPC ............... G02B 27/01; G02B 27/0101; G02B 27/0172; G02B 27/017; G02B 27/0103; G02B 5/208; G02B 2027/0178; G02B 2027/0138; G02B 27/0093; A61B 3/10; A61B 3/14; A61B 3/12; A61B 3/113; A61B 5/163; A61B 5/1122; A61B 5/742; A61B 5/117; G02C 11/10; G02C 11/00
USPC ........... 359/350, 13, 630, 631, 633; 345/7, 8
See application file for complete search history.

(56) References Cited

U.S. PATENT DOCUMENTS 5,285,320 A    2/1994  Hohberg
5,696,550 A   12/1997  Aoki et al.
(Continued)

FOREIGN PATENT DOCUMENTS

WO    WO 2017/053382    3/2017

OTHER PUBLICATIONS

International Search Report and Written Opinion for PCT Application No. PCT/US2016/052814, dated Nov. 18, 2016.
(Continued)

*Primary Examiner* — Jie Lei
(74) *Attorney, Agent, or Firm* — Knobbe, Martens, Olson & Bear, LLP

(57) ABSTRACT

Examples of an imaging system for use with a head mounted display (HMD) are disclosed. The imaging system can include a forward-facing imaging camera and a surface of a display of the HMD can include an off-axis diffractive optical element (DOE) or hot mirror configured to reflect light to the imaging camera. The DOE or hot mirror can be segmented. The imaging system can be used for eye tracking, biometric identification, multiscopic reconstruction of the three-dimensional shape of the eye, etc.

16 Claims, 14 Drawing Sheets

(51) Int. Cl.
*A61B 3/14* (2006.01)
*G02B 27/00* (2006.01)
*A61B 5/00* (2006.01)
*A61B 5/11* (2006.01)
*A61B 5/16* (2006.01)
*A61B 5/117* (2016.01)

(52) U.S. Cl.
CPC ....... *A61B 5/117* (2013.01); *G02B 2027/0138* (2013.01); *G02B 2027/0178* (2013.01)

(56) References Cited

U.S. PATENT DOCUMENTS

| | | | |
|---|---|---|---|
| 6,433,760 | B1 | 8/2002 | Vaissie et al. |
| 6,850,221 | B1 | 2/2005 | Tickle |
| 7,401,920 | B1 * | 7/2008 | Kranz .................. A61B 3/113 |
| | | | 351/209 |
| 8,950,867 | B2 | 2/2015 | Macnamara |
| 9,081,426 | B2 | 7/2015 | Armstrong |
| 9,215,293 | B2 | 12/2015 | Miller |
| 9,310,559 | B2 | 4/2016 | Macnamara |
| 9,348,143 | B2 | 5/2016 | Gao et al. |
| D758,367 | S | 6/2016 | Natsume |
| 9,417,452 | B2 | 8/2016 | Schowengerdt et al. |
| 9,470,906 | B2 | 10/2016 | Kaji et al. |
| 9,547,174 | B2 | 1/2017 | Gao et al. |
| 9,671,566 | B2 | 6/2017 | Abovitz et al. |
| 9,740,006 | B2 | 8/2017 | Gao |
| 9,791,700 | B2 | 10/2017 | Schowengerdt et al. |
| 9,851,563 | B2 | 12/2017 | Gao et al. |
| 9,857,591 | B2 | 1/2018 | Welch et al. |
| 9,874,749 | B2 | 1/2018 | Bradski |
| 2010/0149073 | A1 * | 6/2010 | Chaum ............... G02B 27/0093 |
| | | | 345/8 |
| 2012/0127062 | A1 | 5/2012 | Bar-Zeev et al. |
| 2013/0082922 | A1 | 4/2013 | Miller |
| 2013/0125027 | A1 | 5/2013 | Abovitz |
| 2013/0322810 | A1 | 12/2013 | Robbins |
| 2014/0003762 | A1 | 1/2014 | Macnamara |
| 2014/0071539 | A1 | 3/2014 | Gao |
| 2014/0177023 | A1 | 6/2014 | Gao et al. |
| 2014/0218468 | A1 | 8/2014 | Gao et al. |
| 2014/0306866 | A1 | 10/2014 | Miller et al. |
| 2015/0016777 | A1 | 1/2015 | Abovitz et al. |
| 2015/0103306 | A1 | 4/2015 | Kaji et al. |
| 2015/0178939 | A1 | 6/2015 | Bradski et al. |
| 2015/0205126 | A1 | 7/2015 | Schowengerdt |
| 2015/0222883 | A1 | 8/2015 | Welch |
| 2015/0222884 | A1 | 8/2015 | Cheng |
| 2015/0268415 | A1 | 9/2015 | Schowengerdt et al. |
| 2015/0302652 | A1 | 10/2015 | Miller et al. |
| 2015/0346490 | A1 | 12/2015 | TeKolste et al. |
| 2015/0346495 | A1 | 12/2015 | Welch et al. |
| 2016/0011419 | A1 | 1/2016 | Gao |
| 2016/0026253 | A1 | 1/2016 | Bradski et al. |
| 2018/0046859 | A1 | 2/2018 | Jarvenpaa |
| 2018/0164627 | A1 | 6/2018 | Oh |

OTHER PUBLICATIONS

International Preliminary Report on Patentability for PCT Application No. PCT/US2016/052814, dated Mar. 27, 2018.

* cited by examiner

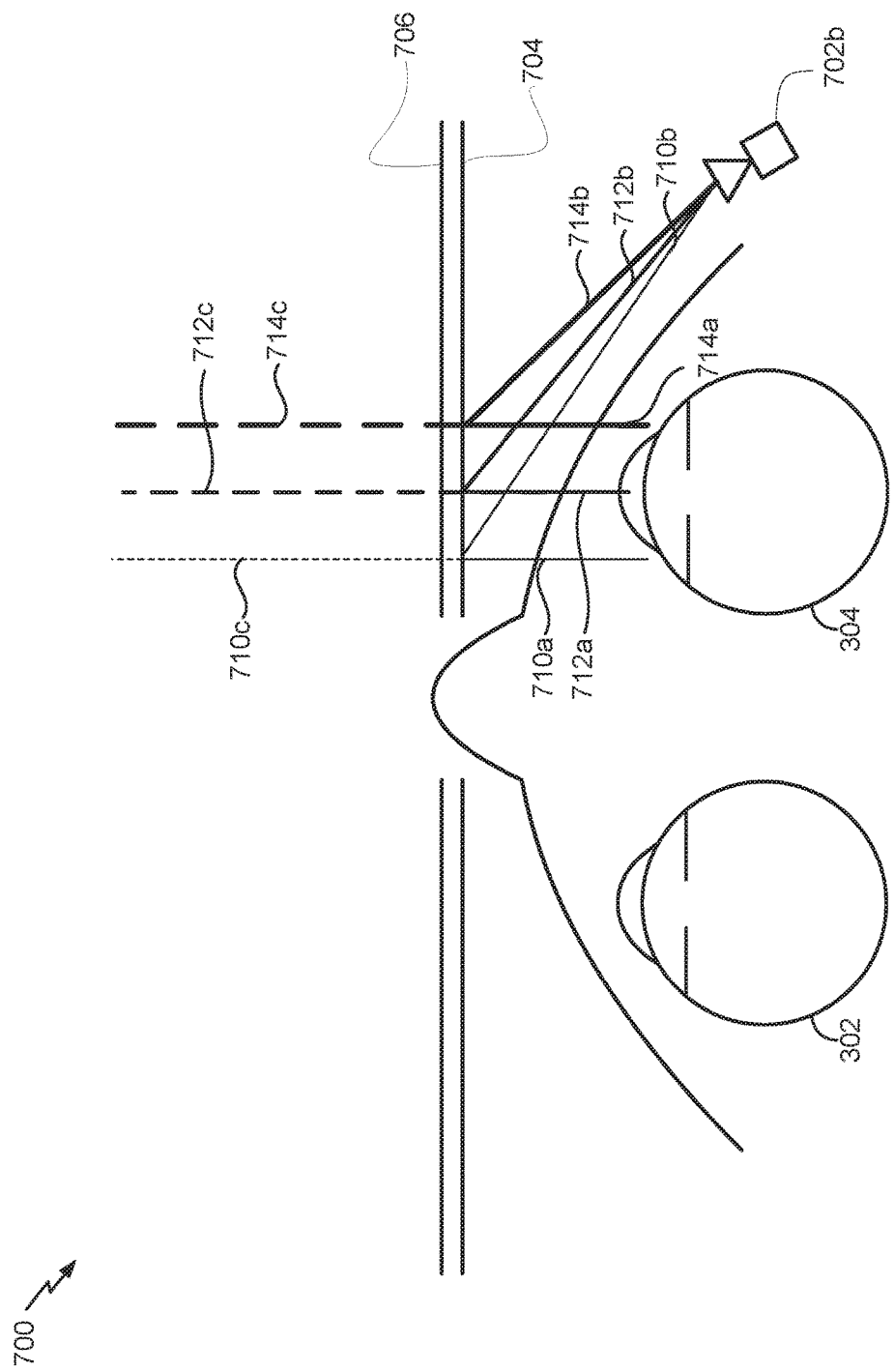

EYE IMAGING WITH AN OFF-AXIS IMAGER

CROSS-REFERENCE TO RELATED APPLICATIONS

This application claims the benefit of priority under 35 U.S.C. § 119(e) to U.S. Provisional Application No. 62/222,671, filed on Sep. 23, 2015, entitled "EYE IMAGING WITH AN OFF-AXIS IMAGER," which is hereby incorporated by reference herein in its entirety.

BACKGROUND

Field

The present disclosure relates to virtual reality and augmented reality imaging and visualization systems and in particular to imaging systems for acquiring images of an eye.

Description of the Related Art

Modern computing and display technologies have facilitated the development of systems for so called "virtual reality" or "augmented reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user; or a mixed reality "MR," relating to merging real and virtual worlds to produce new environment where physical and virtual objects co-exist and interact in real time. As it turns out, the human visual perception system is very complex, and producing a VR, AR, or MR technology that facilitates a comfortable, natural-feeling, rich presentation of virtual image elements amongst other virtual or real-world imagery elements is challenging. Systems and methods disclosed herein address various challenges related to VR, AR, and MR technology.

SUMMARY

An embodiment of a head mounted display (HMD) configured to be worn on a head of a user is disclosed. The HMD comprises: a frame comprising a pair of ear stems; a pair of optical elements supported by the frame such that each of the pair of optical elements is capable of being disposed forward of an eye of the user; a forward-facing imager mounted to one of the pair of ear stems; and a reflective element disposed in or on one of the pair of optical elements, the reflective element configured to reflect infrared light toward the forward-facing imager, which is configured to receive the infrared light reflected by the reflective element. Each of the pair of optical elements can be transparent to visible light. The reflective element can include a plurality of segments that have the same or different optical properties. The imager can be configured to acquire imagery of an eye of a wearer of the HMD. The HMD can include a processor that analyzes imagery acquired by the imager for eye tracking, biometric identification, multiscopic reconstruction of a shape of the eye, estimating an accommodation state of the eye, or imaging the retina of the eye.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIGS. 7A-7F schematically illustrate examples of imaging systems comprising a forward-facing camera that images a wearer's eye using a reflective off-axis Diffractive Optical Element (DOE).

Figure 1:
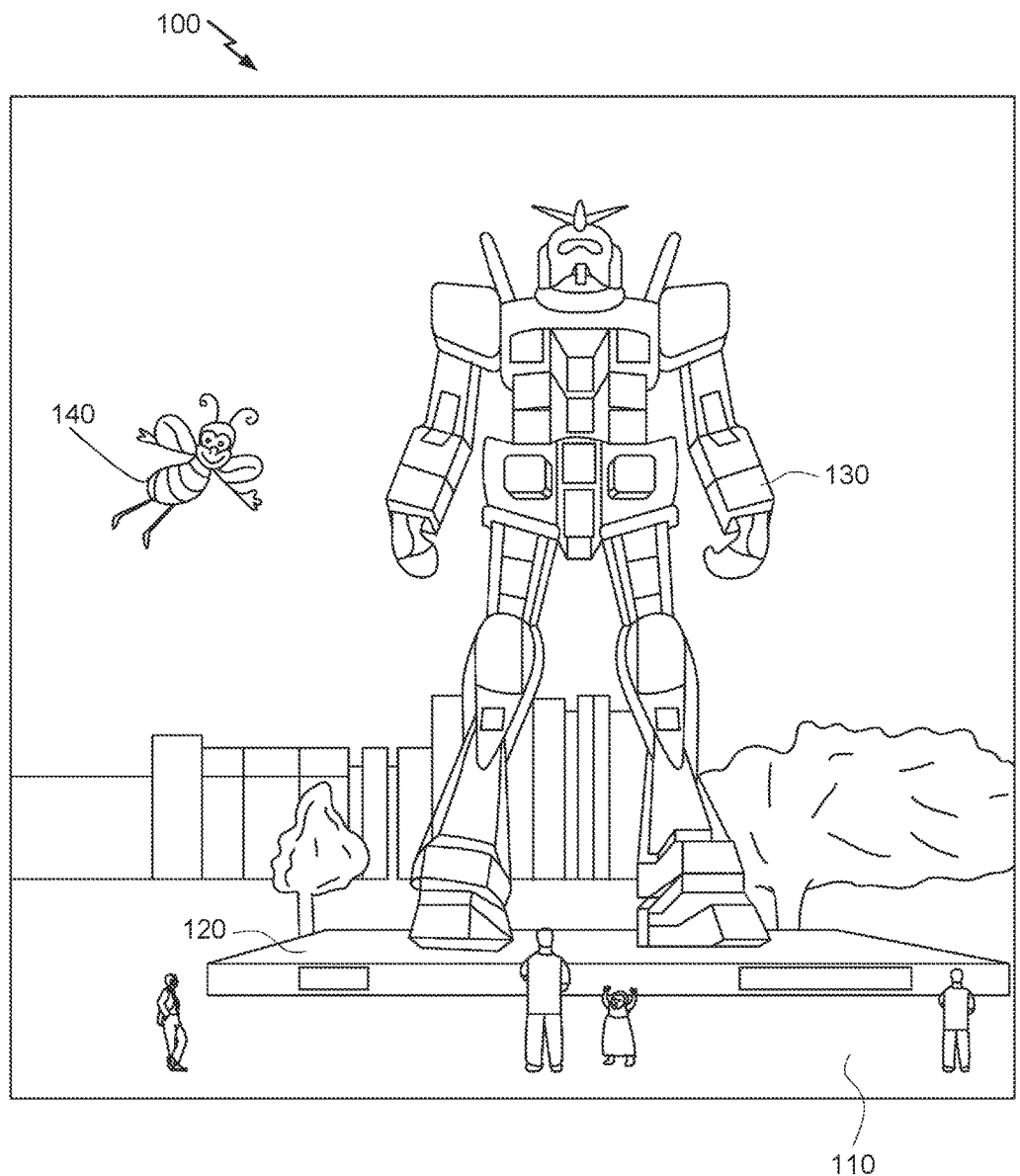
FIG. 1 depicts an illustration of an augmented reality scenario with certain virtual reality objects, and certain actual reality objects viewed by a person.

Throughout the drawings, reference numbers may be re-used to indicate correspondence between referenced elements. The drawings are provided to illustrate example embodiments described herein and are not intended to limit the scope of the disclosure.

DETAILED DESCRIPTION

Overview

The eyes of a wearer of a head mounted display (HMD) can be imaged using a reflective off-axis Diffractive Optical Element (DOE). In some implementations, the DOE may be a Holographic Optical Element (HOE), an off-axis holographic mirror (OAHM), or an off-axis volumetric diffractive optical element (OAVDOE). The resulting images can be used to track an eye or eyes, image the retina, reconstruct the eye shape in three dimensions, extract biometric information from the eye (e.g., iris identification), etc.

A head mounted display (HMD) might use information about the state of the eyes of the wearer for a variety of purposes. For example, this information can be used for estimating the gaze direction of the wearer or for biometric identification. However, imaging the eyes of a wearer of a HMD can be challenging. The distance between the HMD and the wearer's eyes is short. Furthermore, gaze tracking requires a larger field of view, while biometric identification requires a relatively high number of pixels on target on the iris. For an imaging system which will attempt to accomplish both of these objectives, the requirements of the two tasks are largely at odds. Furthermore, both problems may be further complicated by occlusion by the eyelids and eyelashes.

Embodiments of the imaging systems described herein address some or all of these problems. For example, an imaging system can comprise an imager which is configured to view an eye of a wearer. The imaging system can be mounted in proximity to the wearer's temple (e.g., on a frame of a wearable display system, for example, an ear stem). In some embodiments, a second imager can be used for the wearer's other eye so that each eye is separately imaged. The imager can include an infrared digital camera that is sensitive to infrared radiation. The imager can be mounted so that it is facing forward (in the direction of the wearer's vision), rather than facing backward and directed at the eye. By disposing the imager nearer the ear of the wearer, the weight of the imager may also be nearer the ear, and the HMD may be easier to wear as compared to an HMD where the imager is backward facing and disposed nearer to the front of the HMD. Additionally, by placing the forward-facing imager near the wearer's temple, the distance from the wearer's eye to the imager is roughly twice as large as compared to a backward-facing imager disposed near the front of the HMD. Since the depth of field of an image is roughly proportional to this distance, the depth of field for the forward-facing imager is roughly twice as large as compared to a backward-facing imager. A larger depth of field for the imager can be advantageous for imaging the eye region of wearers having large or protruding noses, brow ridges, etc.

The imager can be positioned to view an inside surface of an otherwise transparent optical element. The optical element can be a portion of a display of an HMD (or a lens in a pair of eyeglasses). The optical element can comprise a surface reflecting a first range of wavelengths while being substantially transmissive to a second range of wavelengths (that is different from the first range of wavelengths). The first range of wavelengths can be in the infrared, and the second range of wavelengths can be in the visible. For example, the optical element can comprise a hot mirror, which reflects infrared light while transmitting visible light. Visible light from the outside world can be transmitted through the optical element and can be perceived by the wearer. In effect, the imaging system acts as if there were a virtual imager directed back toward the wearer's eye. The virtual imager can image virtual infrared light propagated from the wearer's eye through the optical element. The hot mirror (or other DOE described herein) can be disposed on the inside surface of the optical element, on an outside surface of the optical element, or within the optical element (e.g., a volume HOE).

Infrared radiation can include radiation with wavelengths in a range from 700 nm to 10 µm. Infrared radiation can include near-infrared radiation with wavelengths in a range from 700 nm to 1.5 µm. In many implementations, the eye imaging is performed in the near infrared at wavelengths from 700 nm to 900 nm.

3D Display

FIG. 1 depicts an illustration of an augmented reality scenario with certain virtual reality objects, and certain actual reality objects viewed by a person. FIG. 1 depicts an augmented reality scene 100, wherein a user of an AR technology sees a real-world park-like setting 110 featuring people, trees, buildings in the background, and a concrete platform 120. In addition to these items, the user of the AR technology also perceives that he "sees" a robot statue 130 standing upon the real-world platform 120, and a cartoon-like avatar character 140 flying by which seems to be a personification of a bumble bee, even though these elements do not exist in the real world.

In order for a three-dimensional (3-D) display to produce a true sensation of depth, and more specifically, a simulated sensation of surface depth, it is desirable for each point in the display's visual field to generate the accommodative response corresponding to its virtual depth. If the accommodative response to a display point does not correspond to the virtual depth of that point, as determined by the binocular depth cues of convergence and stereopsis, the human eye may experience an accommodation conflict, resulting in unstable imaging, harmful eye strain, headaches, and, in the absence of accommodation information, almost a complete lack of surface depth.

VR, AR, and MR experiences can be provided by display systems having displays in which images corresponding to a plurality of depth planes are provided to a viewer. The images may be different for each depth plane (e.g., provide slightly different presentations of a scene or object) and may be separately focused by the viewer's eyes, thereby helping to provide the user with depth cues based on the accommodation of the eye required to bring into focus different image features for the scene located on different depth plane and/or based on observing different image features on different depth planes being out of focus. As discussed elsewhere herein, such depth cues provide credible perceptions of depth.

Figure 2:
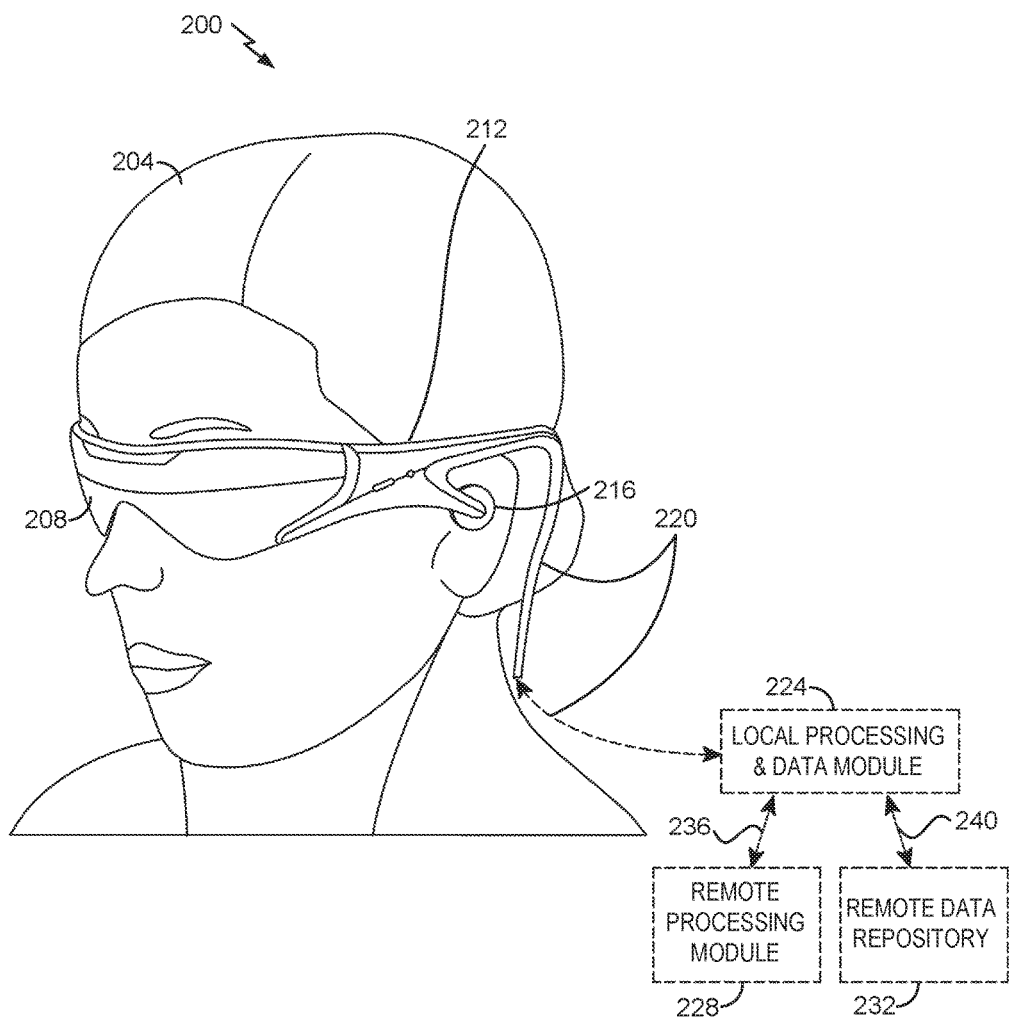
FIG. 2 schematically illustrates an example of a wearable display system.

FIG. 2 illustrates an example of wearable display system 200 that can be used to present a VR, AR, or MR experience to a display system wearer or viewer 204. The display system 200 includes a display 208, and various mechanical and electronic modules and systems to support the functioning of display 208. The display 208 may be coupled to a frame 212, which is wearable by a display system user, wearer, or viewer 204 and which is configured to position the display 208 in front of the eyes of the wearer 204. The display 208 may be a light field display. In some embodiments, a speaker 216 is coupled to the frame 212 and positioned adjacent the ear canal of the user (in some embodiments, another speaker, not shown, is positioned adjacent the other ear canal of the user to provide for stereo/shapeable sound control). The display 208 is operatively coupled 220, such as by a wired lead or wireless connectivity, to a local data processing module 224 which may be mounted in a variety of configurations, such as fixedly attached to the frame 212, fixedly attached to a helmet or hat worn by the user, embedded in headphones, or otherwise removably attached to the user 204 (e.g., in a backpack-style configuration, in a belt-coupling style configuration).

The local processing and data module 224 may comprise a hardware processor, as well as non-transitory digital memory, such as non-volatile memory (e.g., flash memory), both of which may be utilized to assist in the processing, caching, and storage of data. The data may include data (a) captured from sensors (which may be, e.g., operatively coupled to the frame 212 or otherwise attached to the user 204), such as image capture devices (such as cameras), microphones, inertial measurement units, accelerometers, compasses, GPS units, radio devices, and/or gyros; and/or (b) acquired and/or processed using remote processing module 228 and/or remote data repository 232, possibly for passage to the display 208 after such processing or retrieval. The local processing and data module 224 may be operatively coupled to the remote processing module 228 and remote data repository 232 by communication links 236 and/or 240, such as via wired or wireless communication links, such that these remote modules 228, 232 are available as resources to the local processing and data module 224. In addition, remote processing module 228 and remote data repository 232 may be operatively coupled to each other.

In some embodiments, the remote processing module 228 may comprise one or more processors configured to analyze and process data and/or image information such as video information captured by an image capture device. The video data may be stored locally in the local processing and data module 224 and/or in the remote data repository 232. In some embodiments, the remote data repository 232 may comprise a digital data storage facility, which may be available through the internet or other networking configuration in a "cloud" resource configuration. In some embodiments, all data is stored and all computations are performed in the local processing and data module 224, allowing fully autonomous use from a remote module.

The human visual system is complicated and providing a realistic perception of depth is challenging. Without being limited by theory, it is believed that viewers of an object may perceive the object as being three-dimensional due to a combination of vergence and accommodation. Vergence movements (i.e., rolling movements of the pupils toward or away from each other to converge the lines of sight of the eyes to fixate upon an object) of the two eyes relative to each other are closely associated with focusing (or "accommodation") of the lenses of the eyes. Under normal conditions, changing the focus of the lenses of the eyes, or accommodating the eyes, to change focus from one object to another object at a different distance will automatically cause a matching change in vergence to the same distance, under a relationship known as the "accommodation-vergence reflex." Likewise, a change in vergence will trigger a matching change in accommodation, under normal conditions. Display systems that provide a better match between accommodation and vergence may form more realistic or comfortable simulations of three-dimensional imagery.

Figure 3:
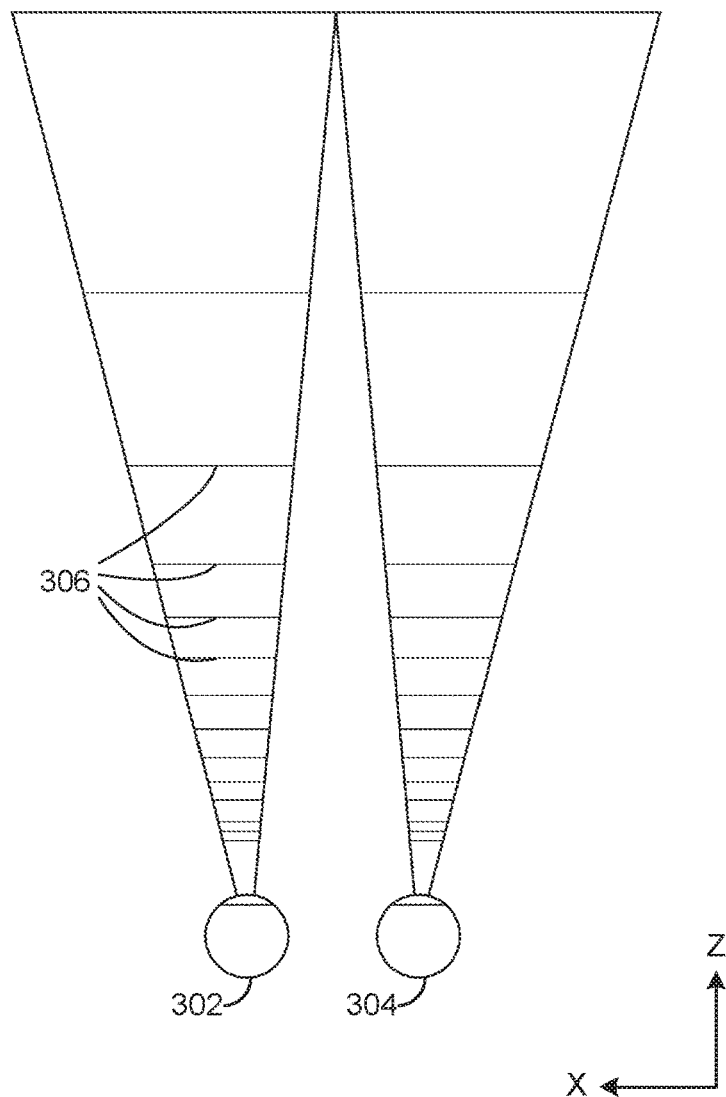
FIG. 3 schematically illustrates aspects of an approach for simulating three-dimensional imagery using multiple depth planes.

FIG. 3 illustrates aspects of an approach for simulating three-dimensional imagery using multiple depth planes. With reference to FIG. 3, objects at various distances from eyes 302 and 304 on the z-axis are accommodated by the eyes 302 and 304 so that those objects are in focus. The eyes 302 and 304 assume particular accommodated states to bring into focus objects at different distances along the z-axis. Consequently, a particular accommodated state may be said to be associated with a particular one of depth planes 306, with an associated focal distance, such that objects or parts of objects in a particular depth plane are in focus when the eye is in the accommodated state for that depth plane. In some embodiments, three-dimensional imagery may be simulated by providing different presentations of an image for each of the eyes 302 and 304, and also by providing different presentations of the image corresponding to each of the depth planes. While shown as being separate for clarity of illustration, it will be appreciated that the fields of view of the eyes 302 and 304 may overlap, for example, as distance along the z-axis increases. In addition, while shown as flat for ease of illustration, it will be appreciated that the contours of a depth plane may be curved in physical space, such that all features in a depth plane are in focus with the eye in a particular accommodated state. Without being limited by theory, it is believed that the human eye typically can interpret a finite number of depth planes to provide depth perception. Consequently, a highly believable simulation of perceived depth may be achieved by providing, to the eye, different presentations of an image corresponding to each of these limited number of depth planes.

Waveguide Stack Assembly

Figure 4:
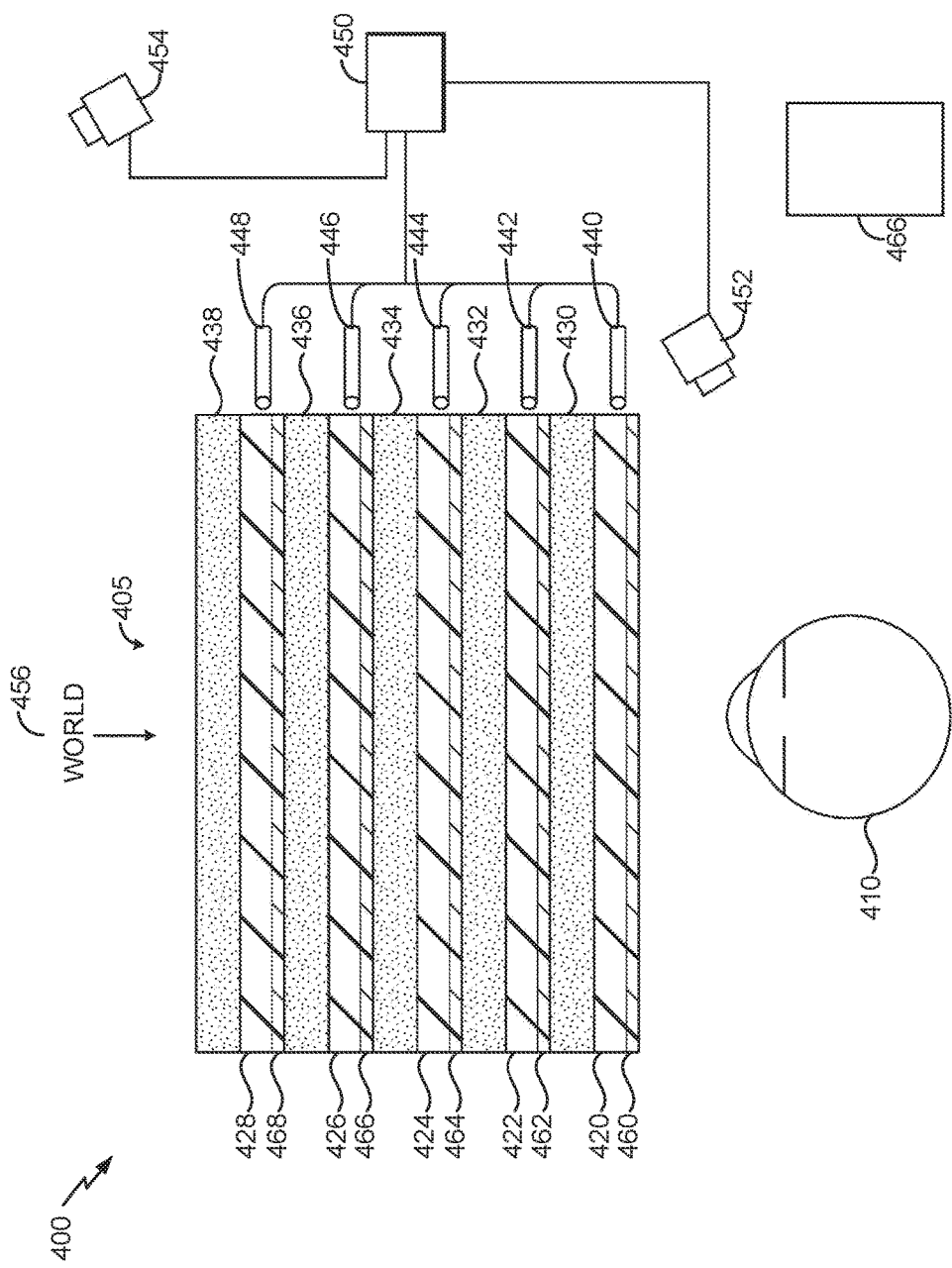
FIG. 4 schematically illustrates an example of a waveguide stack for outputting image information to a user.

FIG. 4 illustrates an example of a waveguide stack for outputting image information to a user. A display system 400 includes a stack of waveguides, or stacked waveguide assembly 405 that may be utilized to provide three-dimensional perception to the eye 410 or brain using a plurality of waveguides 420, 422, 424, 426, 428. In some embodiments, the display system 400 may correspond to system 200 of FIG. 2, with FIG. 4 schematically showing some parts of that system 200 in greater detail. For example, in some embodiments, the waveguide assembly 405 may be integrated into the display 208 of FIG. 2.

With continued reference to FIG. 4, the waveguide assembly 405 may also include a plurality of features 430, 432, 434, 436 between the waveguides. In some embodiments, the features 430, 432, 434, 436 may be lenses. In some embodiments, the features 430, 432, 434, 436 may not be lenses. Rather, they may be spacers (e.g., cladding layers and/or structures for forming air gaps).

The waveguides 420, 422, 424, 426, 428 and/or the plurality of lenses 430, 432, 434, 436 may be configured to send image information to the eye with various levels of wavefront curvature or light ray divergence. Each waveguide level may be associated with a particular depth plane and may be configured to output image information corresponding to that depth plane. Image injection devices 440, 442, 444, 446, 448 may be utilized to inject image information into the waveguides 420, 422, 424, 426, 428, each of which may be configured to distribute incoming light across each respective waveguide, for output toward the eye 410. Light exits an output surface of the image injection devices 440, 442, 444, 446, 448 and is injected into a corresponding input edge of the waveguides 420, 422, 424, 426, 428. In some embodiments, a single beam of light (e.g., a collimated beam) may be injected into each waveguide to output an entire field of cloned collimated beams that are directed toward the eye 410 at particular angles (and amounts of divergence) corresponding to the depth plane associated with a particular waveguide.

In some embodiments, the image injection devices 440, 442, 444, 446, 442 are discrete displays that each produce image information for injection into a corresponding waveguide 420, 422, 424, 426, 428, respectively. In some other embodiments, the image injection devices 440, 442, 446, 446, 448 are the output ends of a single multiplexed display which may, for example, pipe image information via one or more optical conduits (such as fiber optic cables) to each of the image injection devices 440, 442, 444, 446, 448.

A controller 450 controls the operation of the stacked waveguide assembly 405 and the image injection devices 440, 442, 444, 446, 448. In some embodiments, the controller 450 includes programming (e.g., instructions in a non-transitory computer-readable medium) that regulates the timing and provision of image information to the waveguides 420, 422, 424, 426, 428. In some embodiments, the controller 450 may be a single integral device, or a distributed system connected by wired or wireless communication channels. The controller 450 may be part of the processing modules 224 or 228 (illustrated in FIG. 2) in some embodiments. In some embodiments, the controller may be in communication with an inward-facing imaging system 452 (e.g., a digital camera), an outward-facing imaging system 454 (e.g., a digital camera), and/or a user input device 466. The inward-facing imaging system 452 (e.g., a digital camera) can be used to capture images of the eye 410 to, for example, determine the size and/or orientation of the pupil of the eye 410. The outward-facing imaging system 454 can be used to image a portion of the world 456. The user can input commands to the controller 450 via the user input device 466 to interact with the display system 400.

The waveguides 420, 422, 424, 426, 428 may be configured to propagate light within each respective waveguide by total internal reflection (TIR). The waveguides 420, 422, 424, 426, 428 may each be planar or have another shape (e.g., curved), with major top and bottom surfaces and edges extending between those major top and bottom surfaces. In the illustrated configuration, the waveguides 420, 422, 424, 426, 428 may each include light extracting optical elements 460, 462, 464, 466, 468 that are configured to extract light out of a waveguide by redirecting the light, propagating within each respective waveguide, out of the waveguide to output image information to the eye 410. Extracted light may also be referred to as outcoupled light, and light extracting optical elements may also be referred to as outcoupling optical elements. An extracted beam of light is outputted by the waveguide at locations at which the light propagating in the waveguide strikes a light redirecting element. The light extracting optical elements (460, 462, 464, 466, 468 may, for example, be reflective and/or diffractive optical features. While illustrated disposed at the bottom major surfaces of the waveguides 420, 422, 424, 426, 428 for ease of description and drawing clarity, in some embodiments, the light extracting optical elements 460, 462, 464, 466, 468 may be disposed at the top and/or bottom major surfaces, and/or may be disposed directly in the volume of the waveguides 420, 422, 424, 426, 428. In some embodiments, the light extracting optical elements 460, 462, 464, 466, 468 may be formed in a layer of material that is attached to a transparent substrate to form the waveguides 420, 422, 424, 426, 428. In some other embodiments, the waveguides 420, 422, 424, 426, 428 may be a monolithic piece of material and the light extracting optical elements 460, 462, 464, 466, 468 may be formed on a surface and/or in the interior of that piece of material.

With continued reference to FIG. 4, as discussed herein, each waveguide 420, 422, 424, 426, 428 is configured to output light to form an image corresponding to a particular depth plane. For example, the waveguide 420 nearest the eye may be configured to deliver collimated light, as injected into such waveguide 420, to the eye 410. The collimated light may be representative of the optical infinity focal plane. The next waveguide up 422 may be configured to send out collimated light which passes through the first lens 430 (e.g., a negative lens) before it can reach the eye 410. First lens 430 may be configured to create a slight convex wavefront curvature so that the eye/brain interprets light coming from that next waveguide up 422 as coming from a first focal plane closer inward toward the eye 410 from optical infinity. Similarly, the third up waveguide 424 passes its output light through both the first lens 430 and second lens 432 before reaching the eye 410. The combined optical power of the first and second lenses 430 and 432 may be configured to create another incremental amount of wavefront curvature so that the eye/brain interprets light coming from the third waveguide 424 as coming from a second focal plane that is even closer inward toward the person from optical infinity than was light from the next waveguide up 422.

The other waveguide layers (e.g., waveguides 426, 428) and lenses (e.g., lenses 434, 436) are similarly configured, with the highest waveguide 428 in the stack sending its output through all of the lenses between it and the eye for an aggregate focal power representative of the closest focal plane to the person. To compensate for the stack of lenses 430, 432, 434, 436 when viewing/interpreting light coming from the world 456 on the other side of the stacked waveguide assembly 405, a compensating lens layer 438 may be disposed at the top of the stack to compensate for the aggregate power of the lens stack 430, 432, 434, 436 below. Such a configuration provides as many perceived focal planes as there are available waveguide/lens pairings. Both the light extracting optical elements 460, 462, 464, 466, 468 of the waveguides 420, 422, 424, 426, 428 and the focusing aspects of the lenses 430, 432, 434, 436 may be static (e.g., not dynamic or electro-active). In some alternative embodiments, either or both may be dynamic using electro-active features.

With continued reference to FIG. 4, the light extracting optical elements 460, 462, 464, 466, 468 may be configured to both redirect light out of their respective waveguides and to output this light with the appropriate amount of divergence or collimation for a particular depth plane associated with the waveguide. As a result, waveguides having different associated depth planes may have different configurations of light extracting optical elements, which output light with a different amount of divergence depending on the associated depth plane. In some embodiments, as discussed herein, the light extracting optical elements 460, 462, 464, 466, 468 may be volumetric or surface features, which may be configured to output light at specific angles. For example, the light extracting optical elements 460, 462, 464, 466, 468 may be volume holograms, surface holograms, and/or diffraction gratings. Light extracting optical elements, such as diffraction gratings, are described in U.S. Patent Publication No. 2015/0178939, published Jun. 25, 2015, which is incorporated by reference herein in its entirety. In some embodiments, the features 430, 432, 434, 436 may not be lenses. Rather, they may simply be spacers (e.g., cladding layers and/or structures for forming air gaps).

In some embodiments, the light extracting optical elements 460, 462, 464, 466, 468 are diffractive features that form a diffraction pattern, or "diffractive optical element" (also referred to herein as a "DOE"). Preferably, the DOE's have a relatively low diffraction efficiency so that only a portion of the light of the beam is deflected away toward the eye 410 with each intersection of the DOE, while the rest continues to move through a waveguide via total internal reflection. The light carrying the image information is thus divided into a number of related exit beams that exit the waveguide at a multiplicity of locations and the result is a fairly uniform pattern of exit emission toward the eye 410 for this particular collimated beam bouncing around within a waveguide.

In some embodiments, one or more DOEs may be switchable between "on" states in which they actively diffract, and "off" states in which they do not significantly diffract. For instance, a switchable DOE may comprise a layer of polymer dispersed liquid crystal, in which microdroplets comprise a diffraction pattern in a host medium, and the refractive index of the microdroplets can be switched to substantially match the refractive index of the host material (in which case the pattern does not appreciably diffract incident light) or the microdroplet can be switched to an index that does not match that of the host medium (in which case the pattern actively diffracts incident light).

In some embodiments, the number and distribution of depth planes and/or depth of field may be varied dynamically based on the pupil sizes and/or orientations of the eyes of the viewer. In some embodiments, an inward-facing imaging system 452 (e.g., a digital camera) may be used to capture images of the eye 410 to determine the size and/or orientation of the pupil of the eye 410. In some embodiments, the inward-facing imaging system 452 may be attached to the frame 212 (as illustrated in FIG. 2) and may be in electrical communication with the processing modules 224 and/or 228, which may process image information from the inward-facing imaging system 452) to determine, e.g., the pupil diameters and/or orientations of the eyes of the user 204.

In some embodiments, the inward-facing imaging system 452 (e.g., a digital camera) can observe the movements of the user, such as the eye movements and the facial movements. The inward-facing imaging system 452 may be used to capture images of the eye 410 to determine the size and/or orientation of the pupil of the eye 410. The inward-facing imaging system 452 can be used to obtain images for use in determining the direction the user is looking (e.g., eye pose) or for biometric identification of the user (e.g., via iris identification). The images obtained by the inward-facing imaging system 452 may be analyzed to determine the user's eye pose and/or mood, which can be used by the display system 400 to decide which audio or visual content should be presented to the user. The display system 400 may also determine head pose (e.g., head position or head orientation) using sensors such as inertial measurement units (IMUs), accelerometers, gyroscopes, etc. The head's pose may be used alone or in combination with eye pose to interact with stem tracks and/or present audio content.

In some embodiments, one camera may be utilized for each eye, to separately determine the pupil size and/or orientation of each eye, thereby allowing the presentation of image information to each eye to be dynamically tailored to that eye. In some embodiments, at least one camera may be utilized for each eye, to separately determine the pupil size and/or eye pose of each eye independently, thereby allowing the presentation of image information to each eye to be dynamically tailored to that eye. In some other embodiments, the pupil diameter and/or orientation of only a single eye 410 (e.g., using only a single camera per pair of eyes) is determined and assumed to be similar for both eyes of the viewer 204.

For example, depth of field may change inversely with a viewer's pupil size. As a result, as the sizes of the pupils of the viewer's eyes decrease, the depth of field increases such that one plane not discernible because the location of that plane is beyond the depth of focus of the eye may become discernible and appear more in focus with reduction of pupil size and commensurate increase in depth of field. Likewise, the number of spaced apart depth planes used to present different images to the viewer may be decreased with decreased pupil size. For example, a viewer may not be able to clearly perceive the details of both a first depth plane and a second depth plane at one pupil size without adjusting the accommodation of the eye away from one depth plane and to the other depth plane. These two depth planes may, however, be sufficiently in focus at the same time to the user at another pupil size without changing accommodation.

In some embodiments, the display system may vary the number of waveguides receiving image information based upon determinations of pupil size and/or orientation, or upon receiving electrical signals indicative of particular pupil sizes and/or orientations. For example, if the user's eyes are unable to distinguish between two depth planes associated with two waveguides, then the controller 450 may be configured or programmed to cease providing image information to one of these waveguides. Advantageously, this may reduce the processing burden on the system, thereby increasing the responsiveness of the system. In embodiments in which the DOEs for a waveguide are switchable between on and off states, the DOEs may be switched to the off state when the waveguide does receive image information.

In some embodiments, it may be desirable to have an exit beam meet the condition of having a diameter that is less than the diameter of the eye of a viewer. However, meeting this condition may be challenging in view of the variability in size of the viewer's pupils. In some embodiments, this condition is met over a wide range of pupil sizes by varying the size of the exit beam in response to determinations of the size of the viewer's pupil. For example, as the pupil size decreases, the size of the exit beam may also decrease. In some embodiments, the exit beam size may be varied using a variable aperture.

The display system 400 can include an outward-facing imaging system 454 (e.g., a digital camera) that images a portion of the world 456. This portion of the world 456 may be referred to as the field of view (FOV) and the imaging system 454 is sometimes referred to as an FOV camera. The entire region available for viewing or imaging by a viewer 204 may be referred to as the field of regard (FOR). The FOR may include 4π steradians of solid angle surrounding the display system 400. In some implementations of the display system 400, the FOR may include substantially all of the solid angle around a user 204 of the display system 400, because the user 204 can move their head and eyes to look at objects surrounding the user (in front, in back, above, below, or on the sides of the user). Images obtained from the outward-facing imaging system 454 can be used to track gestures made by the user (e.g., hand or finger gestures), detect objects in the world 456 in front of the user, and so forth.

The display system 400 can include a user input device 466 by which the user can input commands to the controller 450 to interact with the display system 400. For example, the user input device 466 can include a trackpad, a touchscreen, a joystick, a multiple degree-of-freedom (DOF) controller, a capacitive sensing device, a game controller, a keyboard, a mouse, a directional pad (D-pad), a wand, a haptic device, a totem (e.g., functioning as a virtual user input device), and so forth. In some cases, the user may use a finger (e.g., a thumb) to press or swipe on a touch-sensitive input device to provide input to the display system 400 (e.g., to provide user input to a user interface provided by the display system 400). The user input device 466 may be held by the user's hand during the use of the display system 400. The user input device 466 can be in wired or wireless communication with the display system 400.

Figure 5:
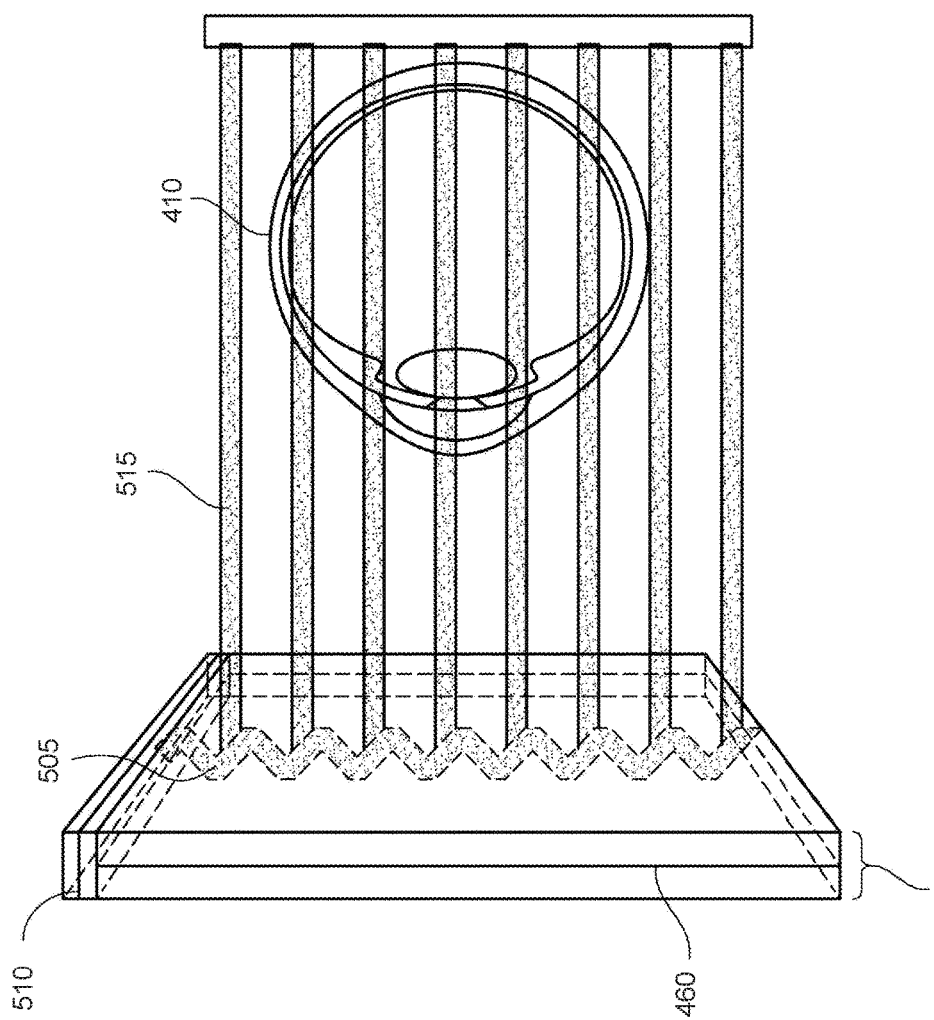
FIG. 5 shows example exit beams that may be outputted by a waveguide.

FIG. 5 shows an example of exit beams outputted by a waveguide. One waveguide is illustrated, but it will be appreciated that other waveguides in the waveguide assembly 405 may function similarly, where the waveguide assembly 405 includes multiple waveguides. Light 505 is injected into the waveguide 420 at the input edge 510 of the waveguide 420 and propagates within the waveguide 420 by TIR. At points where the light 505 impinges on the DOE 460, a portion of the light exits the waveguide as exit beams 515. The exit beams 515 are illustrated as substantially parallel but they may also be redirected to propagate to the eye 410 at an angle (e.g., forming divergent exit beams), depending on the depth plane associated with the waveguide 420. It will be appreciated that substantially parallel exit beams may be indicative of a waveguide with light extracting optical elements that outcouple light to form images that appear to be set on a depth plane at a large distance (e.g., optical infinity) from the eye 410. Other waveguides or other sets of light extracting optical elements may output an exit beam pattern that is more divergent, which would require the eye 410 to accommodate to a closer distance to bring it into focus on the retina and would be interpreted by the brain as light from a distance closer to the eye 410 than optical infinity.

Figure 6:
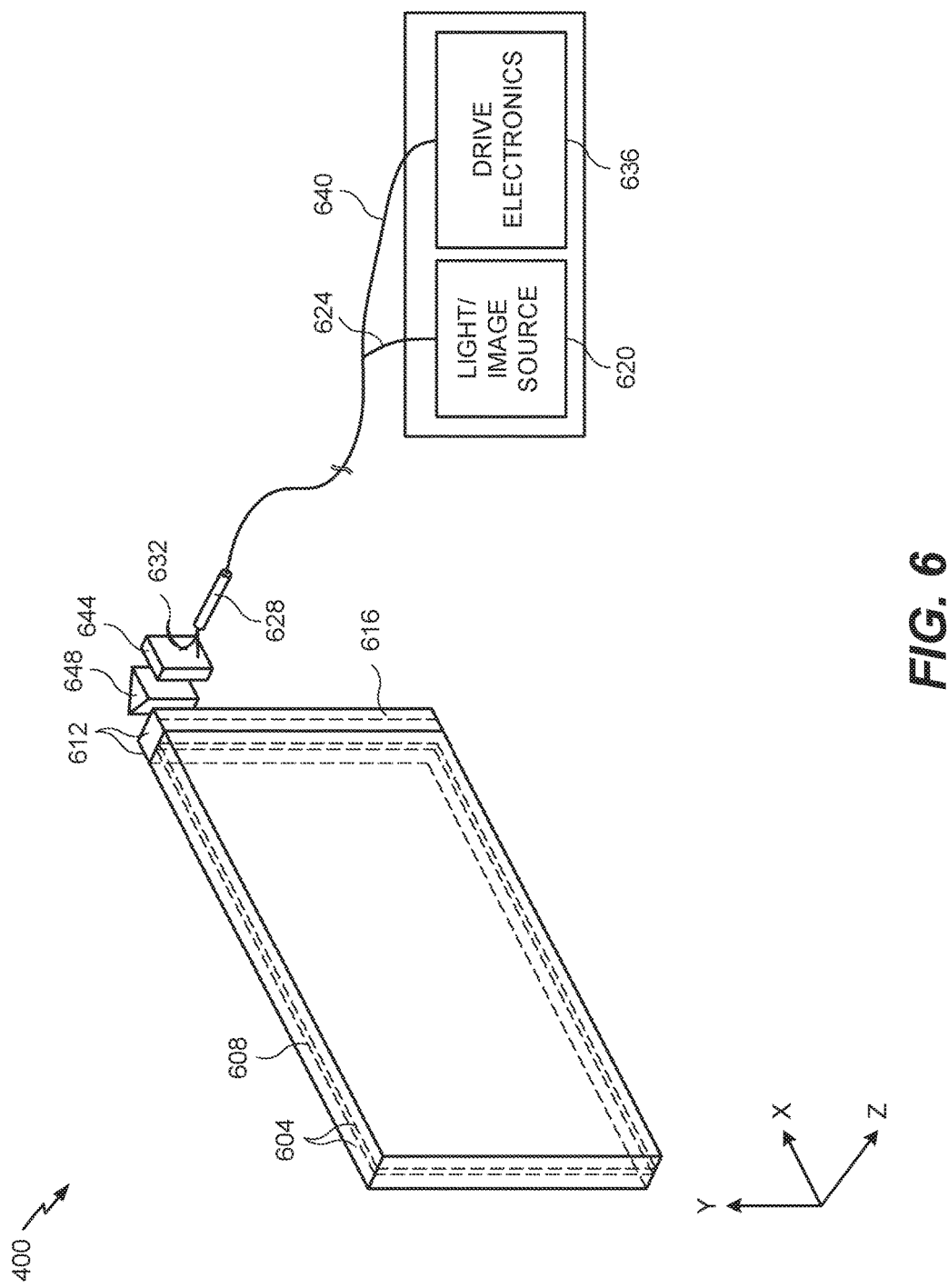
FIG. 6 is a schematic diagram showing a display system including a waveguide apparatus, an optical coupler subsystem to optically couple light to or from the waveguide apparatus, and a control subsystem, used in the generation of a multi-focal volumetric display, image, or light field.

FIG. 6 shows another example of the display system 400 including a waveguide apparatus, an optical coupler subsystem to optically couple light to or from the waveguide apparatus, and a control subsystem. The display system 400 can be used to generate a multi-focal volumetric, image, or light field. The display system 400 can include one or more primary planar waveguides 604 (only one is shown in FIG. 6) and one or more DOEs 608 associated with each of at least some of the primary waveguides 604. The planar waveguides 604 can be similar to the waveguides 420, 422, 424, 426, 428 discussed with reference to FIG. 4. The optical system may employ a distribution waveguide apparatus, to relay light along a first axis (vertical or Y-axis in view of FIG. 6), and expand the light's effective exit pupil along the first axis (e.g., Y-axis). The distribution waveguide apparatus, may, for example include a distribution planar waveguide 612 and at least one DOE 616 (illustrated by double dash-dot line) associated with the distribution planar waveguide 612. The distribution planar waveguide 612 may be similar or identical in at least some respects to the primary planar waveguide 604, having a different orientation therefrom. Likewise, the at least one DOE 616 may be similar or identical in at least some respects to the DOE 608. For example, the distribution planar waveguide 612 and/or DOE 616 may be comprised of the same materials as the primary planar waveguide 604 and/or DOE 608, respectively. The optical system shown in FIG. 6 can be integrated into the wearable display system 200 shown in FIG. 2.

The relayed and exit-pupil expanded light is optically coupled from the distribution waveguide apparatus into the one or more primary planar waveguides 604. The primary planar waveguide 662 relays light along a second axis, preferably orthogonal to first axis, (e.g., horizontal or X-axis in view of FIG. 6). Notably, the second axis can be a non-orthogonal axis to the first axis. The primary planar waveguide 604 expands the light's effective exit path along that second axis (e.g., X-axis). For example, the distribution planar waveguide 612 can relay and expand light along the vertical or Y-axis, and pass that light to the primary planar waveguide 604 which relays and expands light along the horizontal or X-axis.

The display system 400 may include one or more sources of colored light (e.g., red, green, and blue laser light) 620 which may be optically coupled into a proximal end of a single mode optical fiber 624. A distal end of the optical fiber 624 may be threaded or received through a hollow tube 628 of piezoelectric material. The distal end protrudes from the tube 628 as fixed-free flexible cantilever 632. The piezoelectric tube 628 can be associated with four quadrant electrodes (not illustrated). The electrodes may, for example, be plated on the outside, outer surface or outer periphery or diameter of the tube 628. A core electrode (not illustrated) is also located in a core, center, inner periphery or inner diameter of the tube 628.

Drive electronics 636, for example electrically coupled via wires 640, drive opposing pairs of electrodes to bend the piezoelectric tube 628 in two axes independently. The protruding distal tip of the optical fiber 624 has mechanical modes of resonance. The frequencies of resonance can depend upon a diameter, length, and material properties of the optical fiber 624. By vibrating the piezoelectric tube 628 near a first mode of mechanical resonance of the fiber cantilever 632, the fiber cantilever 632 is caused to vibrate, and can sweep through large deflections.

By stimulating resonant vibration in two axes, the tip of the fiber cantilever 632 is scanned biaxially in an area filling two dimensional (2-D) scan. By modulating an intensity of light source(s) 620 in synchrony with the scan of the fiber cantilever 632, light emerging from the fiber cantilever 632 forms an image. Descriptions of such a set up are provided in U.S. Patent Publication No. 2014/0003762, which is incorporated by reference herein in its entirety.

A component 644 of an optical coupler subsystem collimates the light emerging from the scanning fiber cantilever 632. The collimated light is reflected by mirrored surface 648 into the narrow distribution planar waveguide 612 which contains the at least one diffractive optical element (DOE) 616. The collimated light propagates vertically (relative to the view of FIG. 6) along the distribution planar waveguide 612 by total internal reflection, and in doing so repeatedly intersects with the DOE 616. The DOE 616 preferably has a low diffraction efficiency. This causes a fraction (e.g., 10%) of the light to be diffracted toward an edge of the larger primary planar waveguide 604 at each point of intersection with the DOE 616, and a fraction of the light to continue on its original trajectory down the length of the distribution planar waveguide 612 via TIR.

At each point of intersection with the DOE 616, additional light is diffracted toward the entrance of the primary waveguide 612. By dividing the incoming light into multiple outcoupled sets, the exit pupil of the light is expanded vertically by the DOE 616 in the distribution planar waveguide 612. This vertically expanded light coupled out of distribution planar waveguide 612 enters the edge of the primary planar waveguide 604.

Light entering primary waveguide 604 propagates horizontally (relative to the view of FIG. 6) along the primary waveguide 604 via TIR. As the light intersects with DOE 608 at multiple points as it propagates horizontally along at least a portion of the length of the primary waveguide 604 via TIR. The DOE 608 may advantageously be designed or configured to have a phase profile that is a summation of a linear diffraction pattern and a radially symmetric diffractive pattern, to produce both deflection and focusing of the light. The DOE 608 may advantageously have a low diffraction efficiency (e.g., 10%), so that only a portion of the light of the beam is deflected toward the eye of the view with each intersection of the DOE 608 while the rest of the light continues to propagate through the waveguide 604 via TIR.

At each point of intersection between the propagating light and the DOE 608, a fraction of the light is diffracted toward the adjacent face of the primary waveguide 604 allowing the light to escape the TIR, and emerge from the face of the primary waveguide 604. In some embodiments, the radially symmetric diffraction pattern of the DOE 608 additionally imparts a focus level to the diffracted light, both shaping the light wavefront (e.g., imparting a curvature) of the individual beam as well as steering the beam at an angle that matches the designed focus level.

Accordingly, these different pathways can cause the light to be coupled out of the primary planar waveguide 604 by a multiplicity of DOEs 608 at different angles, focus levels, and/or yielding different fill patterns at the exit pupil. Different fill patterns at the exit pupil can be beneficially used to create a light field display with multiple depth planes. Each layer in the waveguide assembly or a set of layers (e.g., 3 layers) in the stack may be employed to generate a respective color (e.g., red, blue, green). Thus, for example, a first set of three adjacent layers may be employed to respectively produce red, blue and green light at a first focal depth. A second set of three adjacent layers may be employed to respectively produce red, blue and green light at a second focal depth. Multiple sets may be employed to generate a full 3D or 4D color image light field with various focal depths.

Example Optical Systems for Eye Imaging with an Off-Axis Imager

The eyes of the wearer of a head mounted display (HMD) (e.g., the wearable display system 200 shown in FIG. 2) can be imaged using a reflective off-axis Diffractive Optical Element (DOE), which in some implementations may be a Holographic Optical Element (HOE). The resulting images can be used to track an eye or eyes, image the retina, reconstruct the eye shape in three dimensions, extract biometric information from the eye (e.g., iris identification), etc.

There are a variety of reasons why a head mounted display (HMD) might use information about the state of the eyes of the wearer. For example, this information can be used for estimating the gaze direction of the wearer or for biometric identification. This problem is challenging, however, because of the short distance between the HMD and the wearer's eyes. It is further complicated by the fact that gaze tracking requires a larger field of view, while biometric identification requires a relatively high number of pixels on target on the iris. For an imaging system which will attempt to accomplish both of these objectives, the requirements of the two tasks are largely at odds. Finally, both problems are further complicated by occlusion by the eyelids and eyelashes. Embodiments of the imaging systems described herein address some or all of these problems. The various embodiments of the imaging systems 700 described herein with reference to FIGS. 7A-7H can be used with HMD including the display devices described herein (e.g., the wearable display system 200 shown in FIG. 2, the display system 400 shown in FIGS. 4 and 6).

Figure 7A:
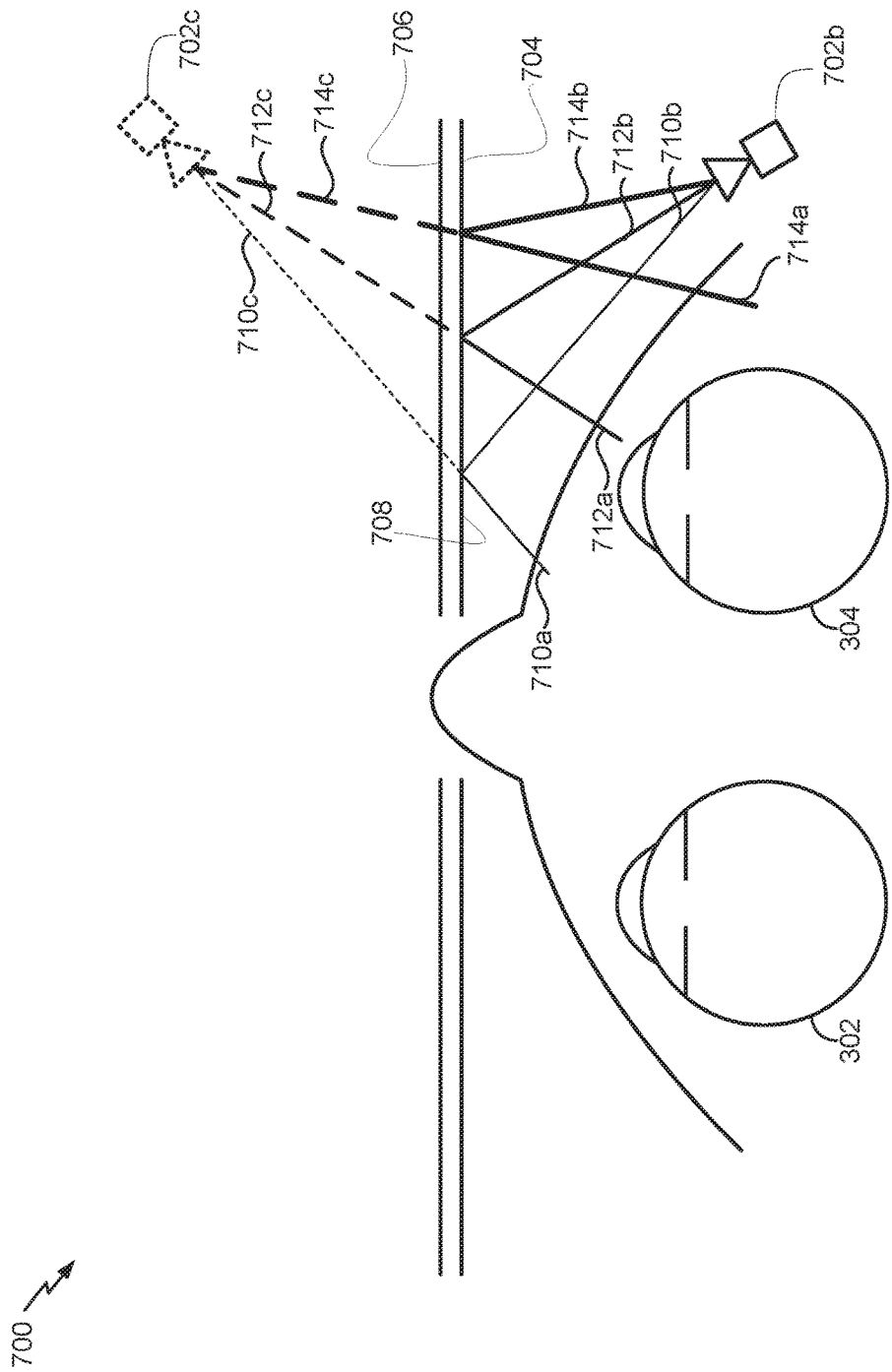

FIG. 7A schematically illustrates an example of an imaging system 700 that comprises an imager 702b which is used to view the eye 304, and which is mounted in proximity to the wearer's temple (e.g., on a frame 212 of the wearable display system 200, for example, an ear stem). In other embodiments, a second imager is used for the wearer's other eye 302 so that each eye is separately imaged. The imager 702b can include an infrared digital camera that is sensitive to infrared radiation. The imager 702b is mounted so that it is facing forward (in the direction of the wearer's vision), rather than facing backward and directed at the eye 304 (as with the camera 452 shown in FIG. 4). By disposing the imager 702b nearer the ear of the wearer, the weight of the imager 702b is also nearer the ear, and the HMD may be easier to wear as compared to an HMD where the imager is backward facing and disposed nearer to the front of the HMD (e.g., close to the display 208). Additionally, by placing the forward-facing imager 702b near the wearer's temple, the distance from the wearer's eye 304 to the imager is roughly twice as large as compared to a backward-facing imager disposed near the front of the HMD (e.g., compare with the camera 452 shown in FIG. 4). Since the depth of field of an image is roughly proportional to this distance, the depth of field for the forward-facing imager 702b is roughly twice as large as compared to a backward-facing imager. A larger depth of field for the imager 702b can be advantageous for imaging the eye region of wearers having large or protruding noses, brow ridges, etc.

The imager 702b is positioned to view an inside surface 704 of an otherwise transparent optical element 706. The optical element 706 can be a portion of the display 208 of an HMD (or a lens in a pair of eyeglasses). The optical element can be transmissive to at least 10%, 20%, 30%, 40%, 50%, or more of visible light incident on the optical element. In other embodiments, the optical element 706 need not be transparent (e.g., in a virtual reality display). The optical element 706 can comprise a reflective element 708. The reflective element 708 can be a surface reflecting a first range of wavelengths while being substantially transmissive to a second range of wavelengths (that is different from the first range of wavelengths). The first range of wavelengths can be in the infrared, and the second range of wavelengths can be in the visible. For example, the reflective element 708 can comprise a hot mirror, which reflects infrared light while transmitting visible light. In such embodiments, infrared light 710a, 712a, 714a from the wearer propagates to and reflects from the optical element 706, resulting in reflected infrared light 710b, 712b, 714b which can be imaged by the imager 702b. In some embodiments, the imager 702b can be sensitive to or able to capture at least a subset (such as a non-empty subset and/or a subset of less than all) of the first range of wavelengths reflected by the reflective element 708. For example, the reflective element 708 may reflect infrared light in the a range of 700 nm to 1.5 µm, and the imager 702b may be sensitive to or able to capture near infrared light at wavelengths from 700 nm to 900 nm. As another example, the reflective element 708 may reflect infrared light in the a range of 700 nm to 1.5 µm, and the imager 702b may include a filter that filters out infrared light in the range of 900 nm to 1.5 µm such that the imager 702b can capture near infrared light at wavelengths from 700 nm to 900 nm.

Visible light from the outside world 456 is transmitted through the optical element 706 and can be perceived by the wearer. In effect, the imaging system 700 shown in FIG. 7A acts as if there were a virtual imager 702c directed back toward the wearer's eye 304. The virtual imager 702c can image virtual infrared light 710c, 712c, 714c (shown as dotted lines) propagated from the wearer's eye 304 through the optical element 706. Although the hot mirror (or other DOE described herein) can be disposed on the inside surface 704 of the optical element 706, this is not a limitation. In other embodiments, the hot mirror or DOE can be disposed on an outside surface of the optical element 706 or within the optical element 706 (e.g., a volume HOE).

Figure 7B:
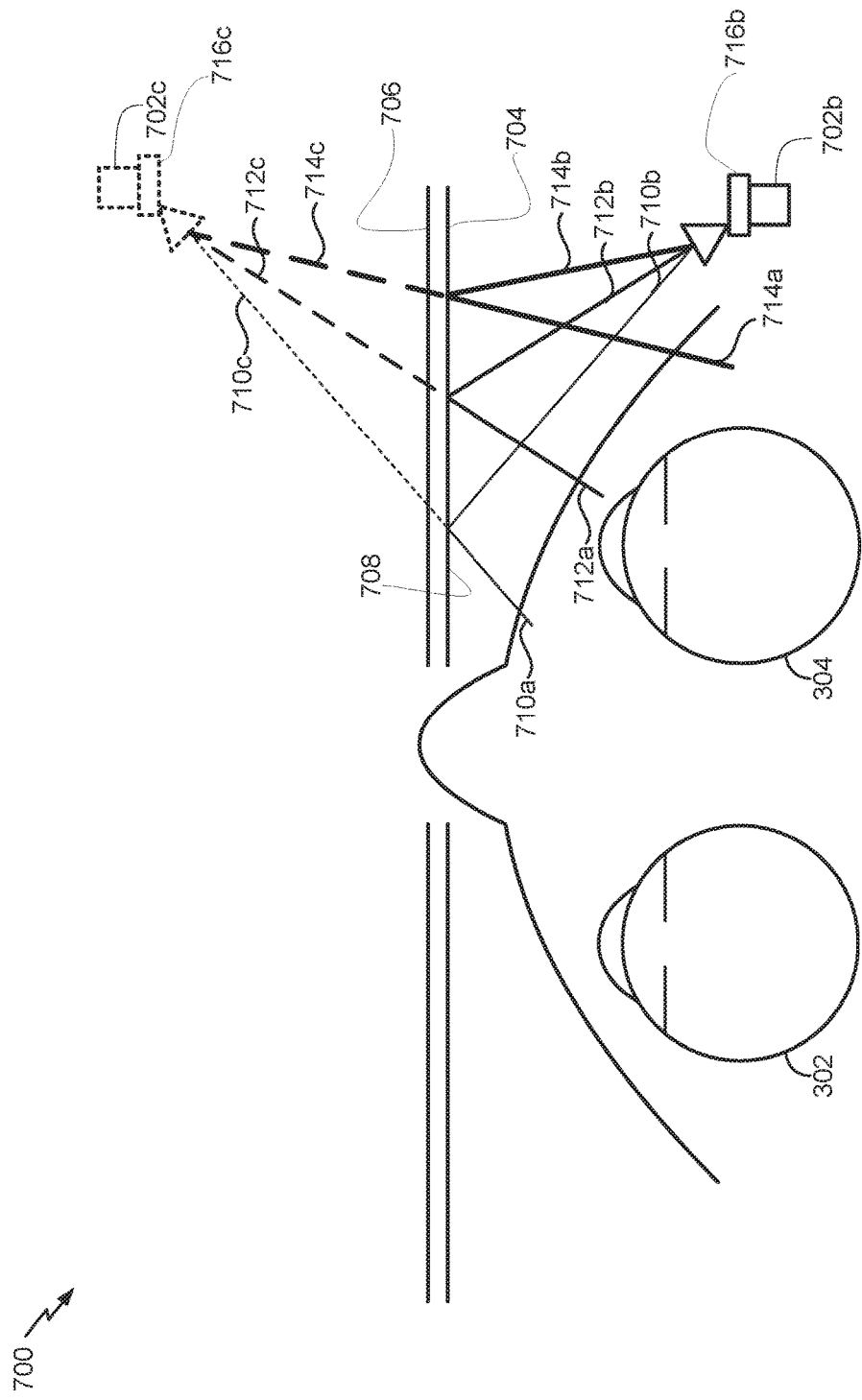

FIG. 7B schematically illustrates another example of the imaging system 700. In this embodiment, perspective distortions may be reduced or eliminated by the use of a perspective control lens assembly 716b (e.g., a shift lens assembly, a tilt lens assembly, or a tilt-shift lens assembly) with the imager 702b. In some embodiments, the perspective control lens assembly 716b may be part of the lens of the imager 702b. The perspective control lens 716b can be configured such that a normal to the imager 702b is substantially parallel to a normal to the region of the surface 704 that includes the DOE (or HOE) or hot mirror. In effect, the imaging system 700 shown in FIG. 7B acts as if there were a virtual imager 702c with a virtual perspective control lens assembly 716c directed back toward the wearer's eye 304.

Figure 7C:
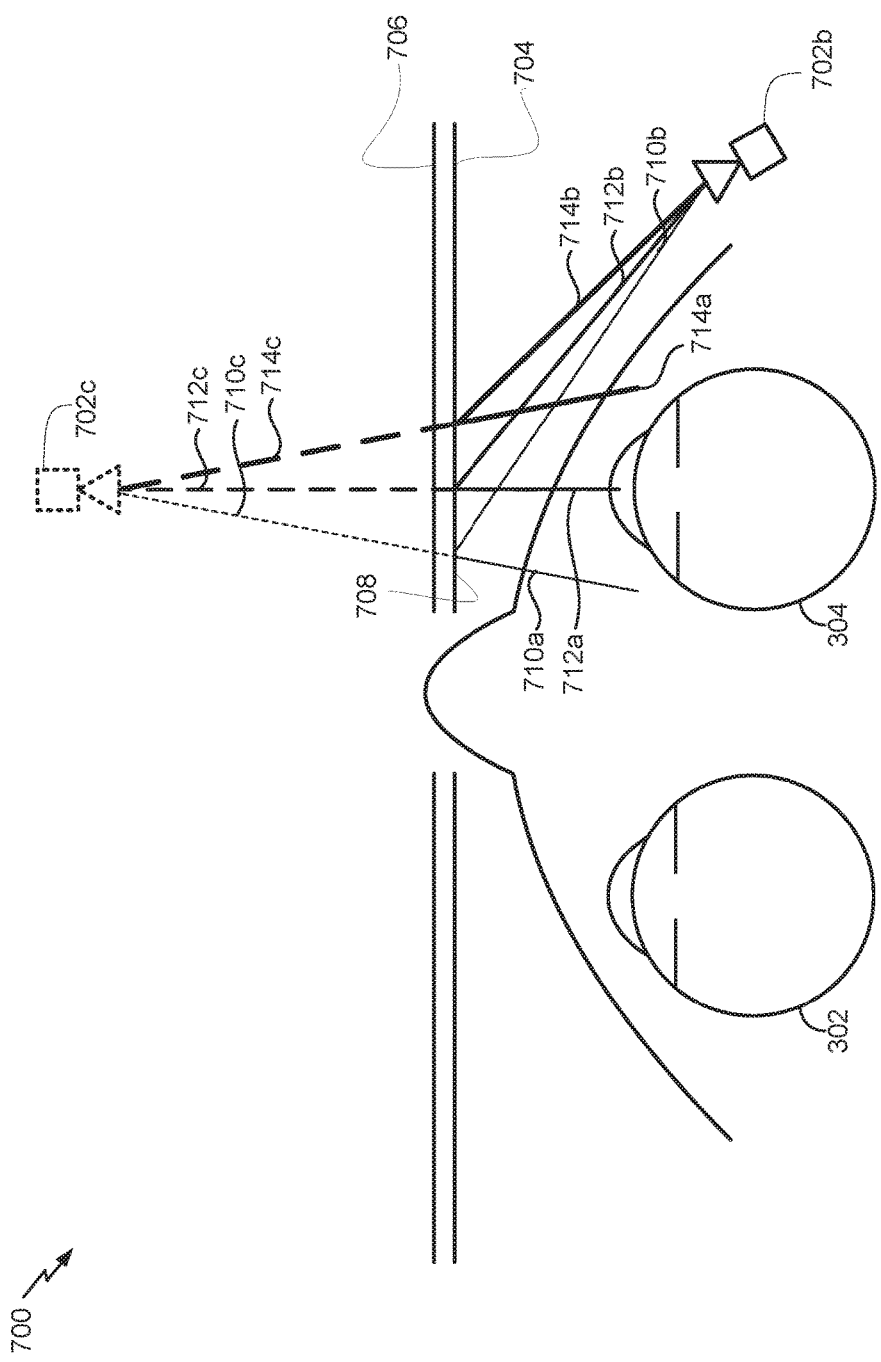

Additionally or alternatively, as schematically shown in FIG. 7C, the reflective element 708 of the optical element 706 may have, on its surface 704, an off axis holographic mirror (OAHM), which is used to reflect light 710a, 712a, 714a to facilitate viewing of the eye 304 by the camera imager 702b which captures reflected light 710b, 712b, 714b. The OAHM 708 may have optical power as well, in which case it can be an off-axis volumetric diffractive optical element (OAVDOE), as schematically shown in FIG. 7D. In the example shown in FIG. 7D, the effective location of the virtual camera 702c is at infinity (and is not shown in FIG. 7D).

Figure 7E:
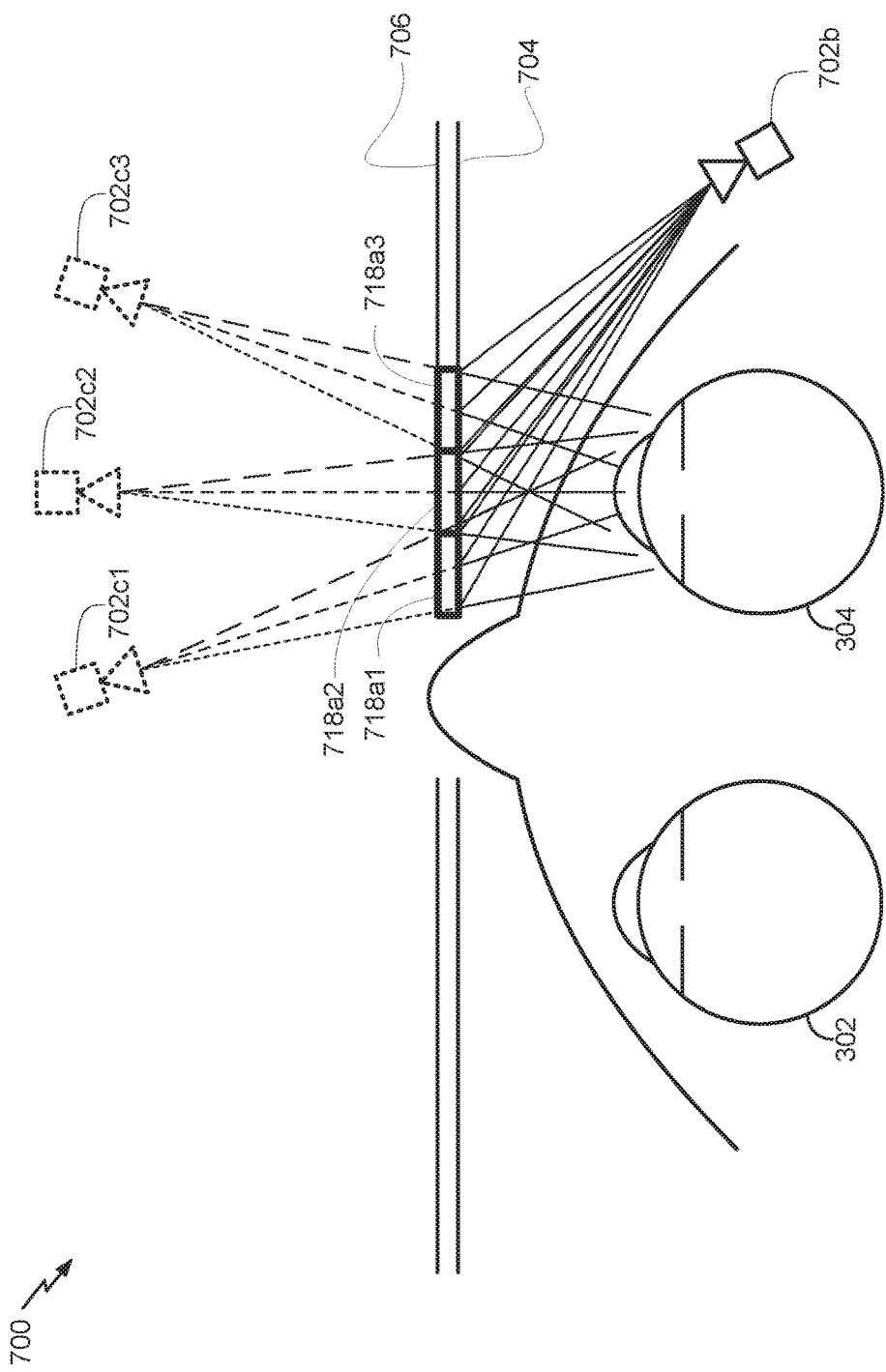

In some embodiments, the HOE (e.g., the OAHM or OAVDOE) can be divided into a plurality of segments. Each of these segments can have different optical properties or characteristics, including, for example, reflection angles at which the segments reflect the incoming (infrared) light or optical power. The segments can be configured so that light is reflected from each segment toward the imager 702b. As a result, the image acquired by the imager 702b will also be divided into a corresponding number of segments, each effectively viewing the eye from a different angle. FIG. 7E schematically illustrates an example of the display system 700 having an OAHM with three segments 718a1, 718a2, 718a3, each of which acts as a respective virtual camera 702c1, 702c2, 702c3 imaging the eye 304 at a different angular location.

Figure 7F:
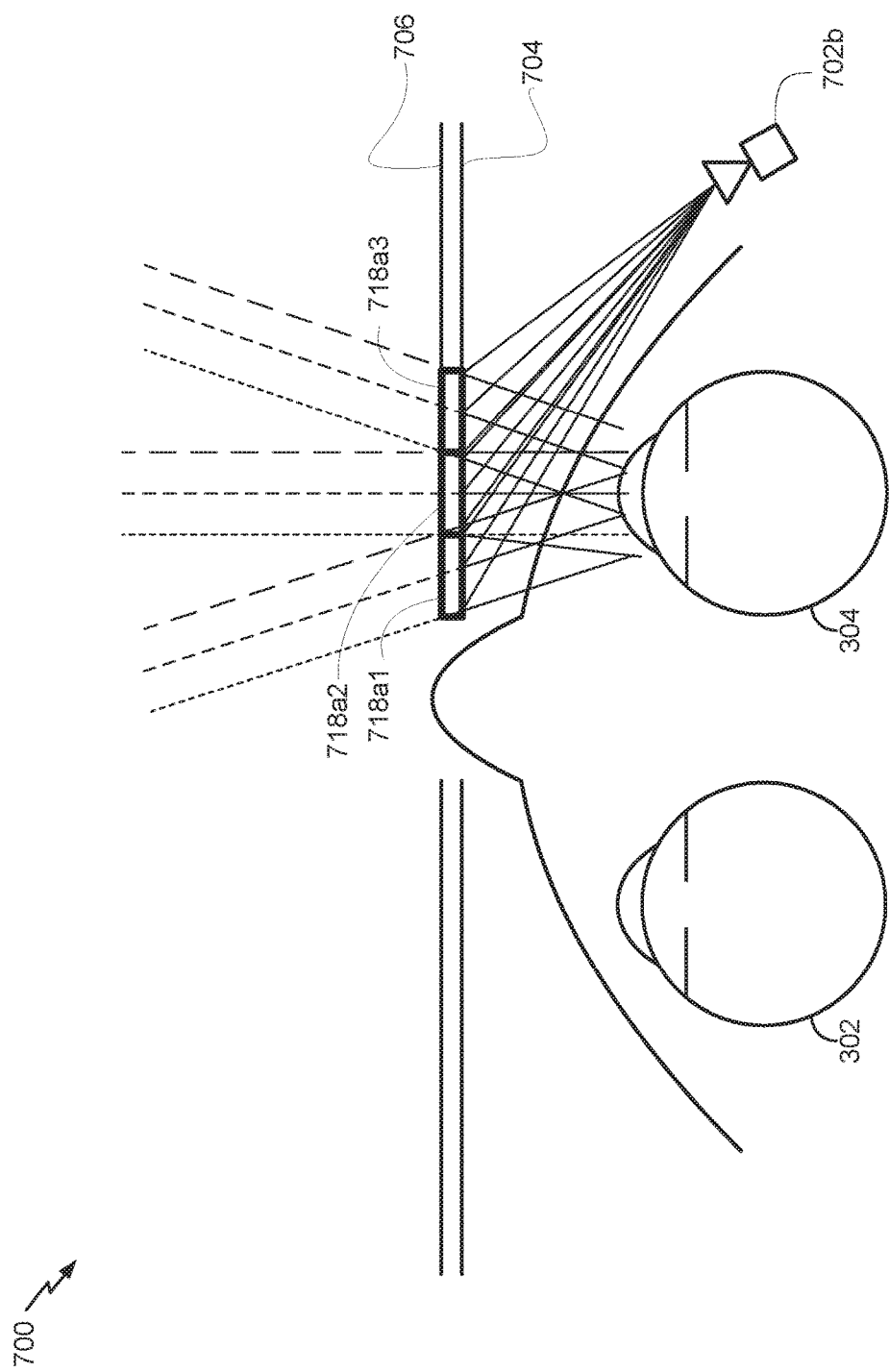

FIG. 7F schematically illustrates another example of the display system 700 having an OAHM with three segments 718a1, 718a2, 718a3, each having optical power (e.g., a segmented OAVDOE), with each segment generating a virtual camera at infinity imaging the eye 304 at a different angular location. Although three segments are schematically illustrated in FIGS. 7E and 7F, this is for illustration and not limitation. In other embodiments, two, four, five, six, seven, eight, nine, or more segments can be utilized. None, some, or all of these segments of the HOE can have optical power.

Figure 7G:
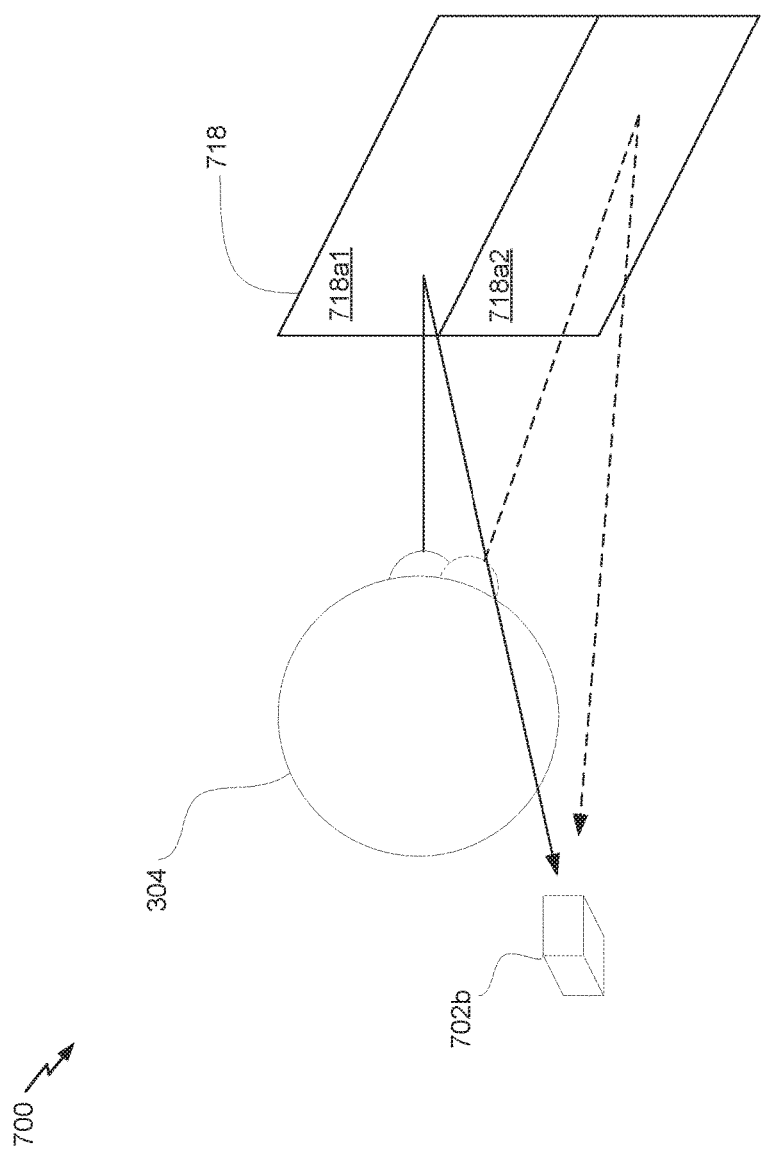
FIGS. 7G and 7H schematically show examples of a DOE having a plurality of segments, each of which can have different optical properties (e.g., reflection angle, optical power, etc.).

The three segments 718a1, 718a2, 718a3 are shown as spaced horizontally across the optical element 706 in FIGS. 7E and 7F. In other embodiments, the segments can be spaced vertically on the optical element 706. For example, FIG. 7G schematically shows a DOE 718 having two vertically spaced segments 718a1 and 718a2, with the segment 718a1 configured to reflect light back toward the imager 702b (which may be in the same general horizontal plane as the segment 718a1), and the segment 718a2 configured to reflect light upwards toward the imager 702b. Similar to bifocal lenses, the arrangement shown in FIG. 7G can be advantageous in allowing the imaging system 700 to use reflection imagery acquired by the imager 702b from the upper segment 718a1 when the wearer is looking forward through the upper portion of the HMD (schematically shown via the solid arrowed line) and to use reflection imagery from the lower segment 718a2 when the wearer is looking downward through the lower portion of the HMD (schematically shown via the dashed arrowed line).

Figure 7H:
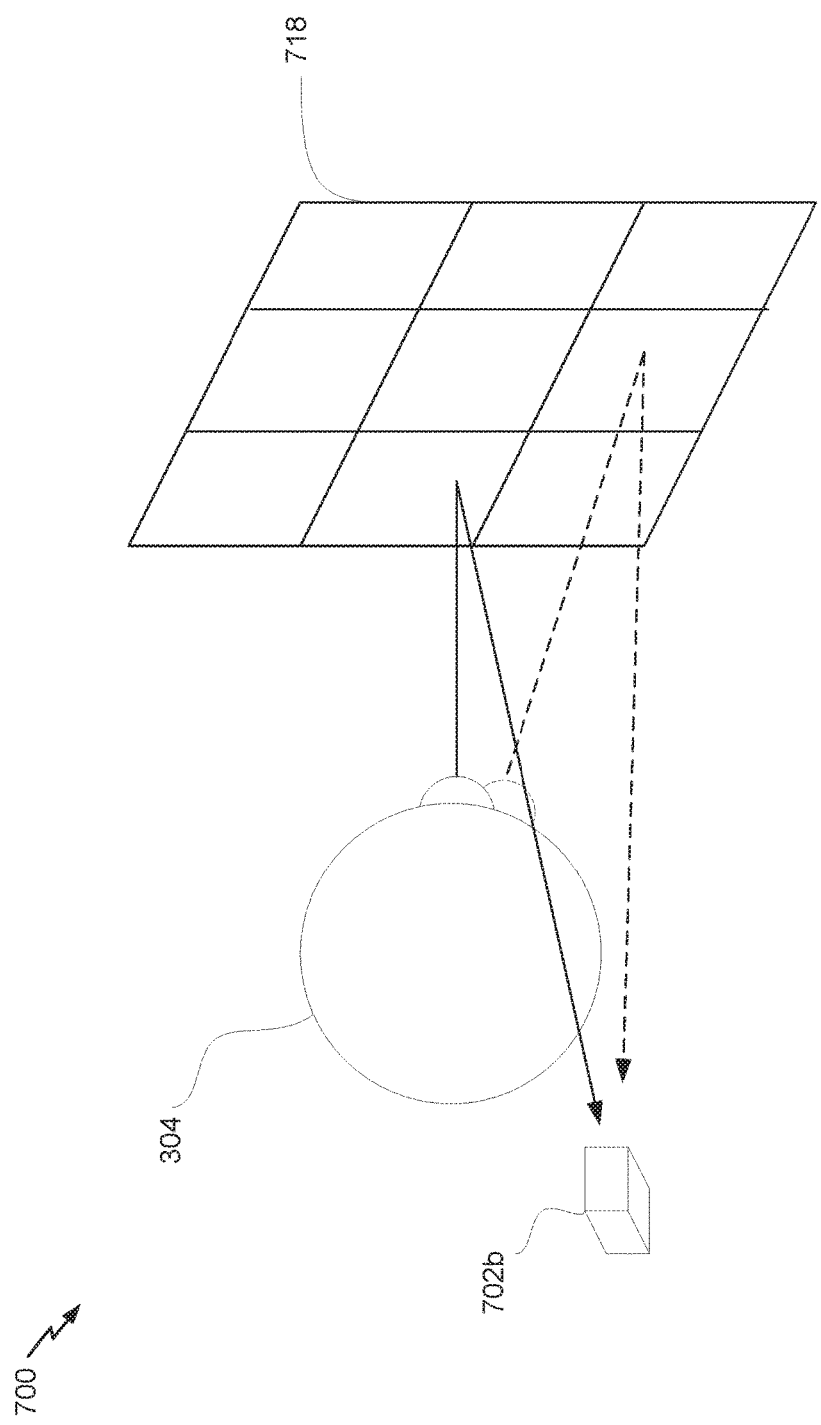

A mix of horizontally spaced and vertically spaced segments can be used in other embodiments. For example, FIG. 7H shows another example of the HOE 718 with a 3×3 array of segments. The imager 702b can acquire reflection data from each of these nine segments, which represent light rays coming from different areas of and angular directions from the eye region. Two example light rays propagating from the eye region to the HOE 718 and reflecting back to the imager 702b are shown as solid and dashed lines. The imaging system 700 (or processing module 224 or 228) can analyze the reflection data from the plurality of segments to multiscopically calculate the three-dimensional shape of the eye or the gaze direction (e.g., eye pose) of the eye.

Embodiments of the optical system 700 utilizing segments may have multiple benefits. For example, the segments can be used individually, by selecting the particular segments which best suit a particular task, or they can be used collectively to multiscopically estimate the three-dimensional shape or pose of the eye. In the former case, this selectivity can be used to, for example, select the image of the wearer's iris which has the least occlusion by eyelids or eyelashes. In the latter case, the three dimensional reconstruction of the eye can be used to estimate orientation (by estimation of, for example, the location of the bulge of the cornea) or accommodation state (by estimation of, for example, the lens induced distortion on the apparent location of the pupil).

Additional Aspects

In a 1st aspect, a head mounted display (HMD) configured to be worn on a head of a user is disclosed. the HMD comprises: a frame comprising a pair of ear stems; a pair of optical elements supported by the frame such that each of the pair of optical elements is capable of being disposed forward of an eye of the user; a forward-facing imager mounted to one of the pair of ear stems; and a reflective element disposed in or on one of the pair of optical elements, the reflective element configured to reflect infrared light toward the forward-facing imager, which is configured to receive the infrared light reflected by the reflective element.

In a 2nd aspect, the HMD of aspect 1, wherein each of the pair of optical elements is transparent to visible light.

In a 3rd aspect, the HMD of aspect 1 or aspect 2, wherein each of the pair of optical elements is configured to display an image to the user.

In a 4th aspect, the HMD of aspect 3, wherein each of the pair of optical elements comprises a light field display.

In a 5th aspect, the HMD of aspect 4, wherein the light field display comprises a waveguide stack configured to output the image to the user.

In a 6th aspect, the HMD of any one of aspects 1 to 5, wherein the reflective element comprises a hot mirror, an off-axis diffractive optical element (DOE), an off-axis holographic mirror (OAHM), or an off-axis volumetric diffractive optical element (OAVDOE).

In a 7th aspect, the HMD of any one of aspects 1 to 6, wherein the reflective element is transmissive to visible light.

In a 8th aspect, the HMD of any one of aspects 1 to 7, wherein the reflective element comprises a plurality of segments, and wherein each segment in the plurality of segments has an optical property that is different from an optical property of at least one other segment in the plurality of segments.

In a 9th aspect, the HMD of aspect 8, wherein the optical property includes a reflection angle or an optical power.

In a 10th aspect, the HMD of aspect 8 or aspect 9, wherein the plurality of segments comprises 2, 3, 4, 5, 6, 7, 8, or 9 segments.

In a 11th aspect, the HMD of any one of aspects 1 to 10, wherein the forward-facing imager is mounted to a temple portion of one of the pair of ear stems.

In a 12th aspect, the HMD of any one of aspects 1 to 11, wherein the imager comprises a perspective control lens assembly.

In a 13th aspect, the HMD of aspect 12, wherein the perspective control lens assembly comprises a shift lens, a tilt lens, or a shift-tilt lens.

In a 14th aspect, a display system is disclosed. The display system comprises: an optical element configured to display an image to a user, the optical element configured to be positioned forward an eye of the user; a forward-facing imager; and a reflective element disposed in or on the optical element, the reflective element configured to reflect toward the forward-facing imager infrared light received from the eye of the user.

In a 15th aspect, the display system of aspect 14, wherein the optical element comprises a light field display.

In a 16th aspect, the display system of aspect 14 or 15, wherein the reflective element comprises a hot mirror, an off-axis diffractive optical element (DOE), an off-axis holographic mirror (OAHM), or an off-axis volumetric diffractive optical element (OAVDOE).

In a 17th aspect, the display system of any one of aspects 14 to 16, wherein the reflective element comprises a plurality of segments having different optical power or different reflection angle.

In a 18th aspect, the display system of any one of aspects 14 to 17, further comprising: non-transitory memory configured to store images of the eye of the user obtained by the forward-facing imager; and a hardware processor in communication with the non-transitory memory, the hardware processor programmed to: access the images of the eye; and perform one or more of the following: track the eye of the user; extract biometric information associated with the eye of the user; reconstruct a shape of a portion of the eye of the user; estimate an accommodation state of the eye of the user; or image a retina, an iris, or other element of the eye of the user.

In a 19th aspect, a head mounted display system is disclosed. The HDM comprises: a frame configured to support the display system according to any one of aspects 14 to 18 such that the optical element is positioned forward a first eye of the user.

In a 20th aspect, the head mounted display system of aspect 19, wherein the frame supports a second display system according to any one of aspects 14 to 18 such that the optical element of the second display system is positioned forward a second eye of the user.

In a 21st aspect, an imaging system is disclosed. The imaging system comprises: a reflective element that reflects light in a first wavelength range; and an imager sensitive to light in a non-empty subset of less than all of the first wavelength range, wherein the imager is configured to be oriented to capture light reflected by the reflective element.

In a 22nd aspect, the imaging system of aspect 21, wherein the reflective element comprises a hot mirror, a holographic optical element (HOE), an off-axis holographic mirror (OAHM), or an off-axis volumetric diffractive optical element (OAVDOE).

In a 23rd aspect, the imaging system of any one of aspects 21-22, wherein the first wavelength range comprises an infrared wavelength range.

In a 24th aspect, the imaging system of any one of aspects 21-23, wherein the imaging system comprises an optical element, wherein the optical element comprises the reflected element, and wherein the optical element is transmissive to at least 50% of visible light incident on the optical element.

In a 25th aspect, the imaging system of any one of aspects 21-24, wherein the reflective element comprises a plurality of segments.

In a 26th aspect, the imaging system of aspect 25, wherein a first segment in the plurality of segments has an optical property that is different from an optical property of a second segment in the plurality of segments.

In a 27th aspect, the imaging system of aspect 26, wherein the optical property of the first segment in the plurality of segments or the optical property of the second segment in the plurality of segments comprises a reflection angle or an optical power.

In a 28th aspect, the imaging system of any one of aspects 25-27, wherein the plurality of segments comprises at least two segments.

In a 29th aspect, the imaging system of any one of aspects 25-28, wherein two of the plurality of segments are arranged horizontally.

In a 30th aspect, the imaging system of any one of aspects 25-29, wherein two of the plurality of segments are arranged vertically.

In a 31st aspect, the imaging system of any one of aspects 25-30, wherein some of the plurality of segments are arranged in a grid.

In a 32nd aspect, the imaging system of any one of aspects 21-31, wherein the imager further comprises a perspective control lens assembly.

In a 33rd aspect, the imaging system of aspect 32, wherein the perspective control lens assembly comprises a shift lens, a tilt lens, or a shift-tilt lens.

In a 34th aspect, an imaging system for indirectly capturing an image of an eye of a user is disclosed. The imaging system comprises: a reflective element that reflects light in a first wavelength range, wherein the reflective element comprises an off-axis holographic mirror (OAHM) or an off-axis volumetric diffractive optical element (OAVDOE), and wherein the reflective element is oriented to reflect light propagating from an eye of a user when the imaging system is placed in front of the eye of the user; and an imager sensitive to light in a non-empty subset of less than all of the first wavelength range, wherein the imager is oriented to image an image of the eye of the user by capturing light propagating from the eye of the user reflected by the reflective element.

In a 35th aspect, the imaging system of aspect 34, wherein the image of the eye of the user imaged by the imager and an image of the eye of the user imaged by a camera placed in front of the eye of the user are indistinguishable.

In a 36th aspect, the imaging system of aspect 35, wherein the image of the eye of the user imaged by the imager is effectively imaged by a camera placed in front of the eye of the user.

In a 37th aspect, the imaging system of any one of aspects 35-36, wherein an effective location of the camera placed in front of the eye of the user is at infinity.

In a 38th aspect, the imaging system of any one of aspects 35-37, wherein the first wavelength range comprises an infrared wavelength range.

In a 39th aspect, the imaging system of any one of aspects 35-38, wherein the imaging system comprises an optical element, wherein the optical element comprises the reflected element, and wherein the optical element is transmissive to at least 50% of visible light incident on the optical element.

In a 40th aspect, the imaging system of any one of aspects 35-39, wherein the reflective element comprises a plurality of segments.

In a 41st aspect, the imaging system of aspect 40, wherein a first segment in the plurality of segments has an optical property that is different from an optical property of a second segment in the plurality of segments.

In a 42nd aspect, the imaging system of aspect 41, wherein the optical property of the first segment in the plurality of segments or the optical property of the second segment in the plurality of segments comprises a reflection angle or an optical power.

In a 43rd aspect, the imaging system of any one of aspects 40-42, wherein the plurality of segments comprises at least two segments.

In a 44th aspect, the imaging system of any one of aspects 40-43, wherein two of the plurality of segments are arranged horizontally.

In a 45th aspect, the imaging system of any one of aspects 40-44, wherein two of the plurality of segments are arranged vertically.

In a 46th aspect, the imaging system of any one of aspects 40-45, wherein some of the plurality of segments are arranged in a grid.

In a 47th aspect, the imaging system of any one of aspects 34-46, wherein the imager further comprises a perspective control lens assembly.

In a 48th aspect, the imaging system of aspect 47, wherein the perspective control lens assembly comprises a shift lens, a tilt lens, or a shift-tilt lens.

In a 49th aspect, an imaging system is disclosed. The imaging system comprises: a display comprising a reflective element that reflects light in a first wavelength range, wherein the reflective element comprises a hot mirror, an off-axis holographic mirror (OAHM), or an off-axis volumetric diffractive optical element (OAVDOE); and an imager sensitive to light in the first wavelength range, wherein the imager is configured to be oriented to capture at least light reflected by the reflective element.

In a 50th aspect, the imaging system of aspect 49, wherein the first wavelength range comprises an infrared wavelength range.

In a 51st aspect, the imaging system of aspect 49 or aspect 50, wherein the display is substantially transmissive to visible light.

In a 52nd aspect, the imaging system of any one of aspects 49-51, wherein the reflective element comprises a plurality of segments, wherein each segment in the plurality of segments has an optical property that is different from an optical property of at least one other segment in the plurality of segments.

In a 53rd aspect, the imaging system of aspect 52, wherein the optical property includes a reflection angle or an optical power.

In a 54th aspect, the imaging system of aspect 52 or aspect 53, wherein the plurality of segments comprises 2, 3, 4, 5, 6, 7, 8, or 9 segments.

In a 55th aspect, the imaging system of any one of aspects 49 to 54, wherein the imager further comprises a perspective control lens assembly.

In a 56th aspect, the imaging system of aspect 55, wherein the perspective control lens assembly comprises a shift lens, a tilt lens, or a shift-tilt lens.

In a 57th aspect, the imaging system of any one of aspects 21 to 56, further comprising: non-transitory data storage configured to store imagery acquired by the imager; and a hardware processor in communication with the non-transitory data storage, the hardware processor programmed with executable instructions to analyze the imager to perform one or more of: eye tracking; biometric identification; multi-scopic reconstruction of a shape of an eye; estimating an accommodation state of an eye; or imaging a retina, iris, or other distinguishing pattern of an eye.

In a 58th aspect, a head mounted display (HMD) is disclosed. The HMD comprises the imaging system of any one of aspects 21 to 57.

In a 59th aspect, the HMD of aspect 58, wherein the HMD comprises a frame having a portion configured to be worn near an ear, and the imager is disposed near the portion.

In a 60th aspect, the HMD of aspect 58 or aspect 59, wherein the imaging system is configured to image a first eye of a wearer, wherein the HMD comprising a second imaging system of any one of aspects 21 to 57, and wherein the second imaging system configured to image a second eye of the wearer.

In a 61st aspect, the HMD of any one of aspects 58-60, wherein the HMD is an augmented reality device (ARD).

In a 62nd aspect, a method of creating a virtual camera is disclosed. The method comprises: providing an imaging system in front of an object to be imaged to create a virtual camera in front of the object, wherein the imaging system comprises: a reflective element that reflects light in a first wavelength range, wherein the reflective element comprises an off-axis holographic mirror (OAHM) or an off-axis volumetric diffractive optical element (OAVDOE), and wherein the reflective element is oriented to reflect light propagating from the object when the imaging system is placed in front of the object; and an imager sensitive to light in a non-empty subset of less than all of the first wavelength range, wherein the imager is oriented to image an image of the object by capturing light propagating from the object reflected by the reflective element, and wherein the image of the object imaged by the imager and an image of the object imaged by a camera in front of the object are indistinguishable.

In a 63rd aspect, the method of aspect 62, wherein the first wavelength range comprises an infrared wavelength range.

In a 64th aspect, the method of any one of aspects 62-63, wherein the imaging system comprises an optical element, wherein the optical element comprises the reflected element, and wherein the optical element is transmissive to at least 50% of visible light incident on the optical element.

In a 65th aspect, the method of any one of aspects 62-64, wherein the reflective element comprises a plurality of segments.

In a 66th aspect, the method of aspect 65, wherein a first segment in the plurality of segments has an optical property that is different from an optical property of a second segment in the plurality of segments.

In a 67th aspect, the method of aspect 66, wherein the optical property of the first segment in the plurality of segments or the optical property of the second segment in the plurality of segments comprises a reflection angle or an optical power.

In a 68th aspect, the method of any one of aspects 65-67, wherein the plurality of segments comprises at least two segments.

In a 69th aspect, the method of any one of aspects 65-68, wherein two of the plurality of segments are arranged horizontally.

In a 70th aspect, the method of any one of aspects 65-69, wherein two of the plurality of segments are arranged vertically.

In a 71st aspect, the method of any one of aspects 65-70, wherein some of the plurality of segments are arranged in a grid.

In a 72nd aspect, the method of any one of aspects 62-71, wherein the imager further comprises a perspective control lens assembly.

In a 73rd aspect, the method of aspect 72, wherein the perspective control lens assembly comprises a shift lens, a tilt lens, or a shift-tilt lens.

In a 74th aspect, a method of imaging an object using a virtual camera is disclosed. The method comprises: providing an imaging system in front of an object to be imaged to create a virtual camera in front of the object, wherein the imaging system comprises: a reflective element that reflects light in a first wavelength range, wherein the reflective element comprises an off-axis holographic mirror (OAHM) or an off-axis volumetric diffractive optical element (OAVDOE), and wherein the reflective element is oriented to reflect light propagating from the object when the imaging system is placed in front of the object; and an imager sensitive to light in a non-empty subset of less than all of the first wavelength range, wherein the imager is oriented to image an image of the object by capturing light propagating from the object reflected by the reflective element; and imaging the object using the virtual camera, comprising: imaging the image of the object by capturing the light propagating from the object reflected by the reflective element, and wherein the image of the object imaged by the imager and an image of the object imaged by a camera in front of the object are indistinguishable.

In a 75th aspect, the method of aspect 74, wherein the first wavelength range comprises an infrared wavelength range.

In a 76th aspect, the method of any one of aspects 74-75, wherein the imaging system comprises an optical element, wherein the optical element comprises the reflected element, and wherein the optical element is transmissive to at least 50% of visible light incident on the optical element.

In a 77th aspect, the method of any one of aspects 74-76, wherein the reflective element comprises a plurality of segments.

In a 78th aspect, the method of aspect 77, wherein a first segment in the plurality of segments has an optical property that is different from an optical property of a second segment in the plurality of segments.

In a 79th aspect, the method of aspect 78, wherein the optical property of the first segment in the plurality of segments or the optical property of the second segment in the plurality of segments comprises a reflection angle or an optical power.

In a 80th aspect, the method of any one of aspects 77-79, wherein the plurality of segments comprises at least two segments.

In a 81st aspect, the method of any one of aspects 77-80, wherein two of the plurality of segments are arranged horizontally.

In a 82nd aspect, the method of any one of aspects 77-81, wherein two of the plurality of segments are arranged vertically.

In a 83rd aspect, the method of any one of aspects 77-82, wherein some of the plurality of segments are arranged in a grid.

In a 84th aspect, the method of any one of aspects 74-83, wherein the imager further comprises a perspective control lens assembly.

In a 85th aspect, the method of aspect 84, wherein the perspective control lens assembly comprises a shift lens, a tilt lens, or a shift-tilt lens.

In a 86th aspect, an imaging assembly is disclosed. The imaging assembly comprises a see through element (e.g., a display), a viewing camera placed so as to view the display, a lens associated with that camera, and a reflective element on the display which renders the display reflective to all or some of the wavelengths to which the display is sensitive.

In a 87th aspect, the assembly of aspect 86, wherein the reflective element comprises a hot mirror, an off-axis holographic mirror (OAHM) or an off-axis volumetric diffractive optical element (OAVDOE).

In a 88th aspect, the assembly of any one of aspects 86-87, wherein the assembly is integrated into a wearable structure such as a pair of glasses or helmet.

In a 89th aspect, the assembly of any of aspects 86-88, wherein the reflective element is segmented.

In a 90th aspect, the assembly of aspect 89, wherein the assembly is configured for use of a segmented OAHM to select the best possible viewing angle for a particular task (e.g., gaze tracking, or biometric identification).

In a 91st aspect, the assembly of any one of aspects 89-90, wherein the assembly is configured for use of a multiplicity of segment sub-images for stereoscopic or multiscopic three dimensional reconstruction of a shape of an eye.

In a 92nd aspect, the assembly of aspect 91, wherein the three dimensional reconstruction of the shape of the eye is used for estimating the accommodation state of the eye.

In a 93rd aspect, the assembly of aspect 92, wherein estimating the accommodation state of the eye comprises comparing an apparent location and shape of a pupil and iris of the eye across multiple images of a same wearer of the assembly.

In a 94th aspect, the assembly of any one of aspects 92-93, wherein estimating the accommodation state of the eye is used to determine a magnification state of the lens.

In a 95th aspect, the assembly of any one of aspects 86-94, wherein the assembly is configured for use of the image segments as input to an information fusion algorithm.

In a 96th aspect, the assembly of aspect 95, the information fusion algorithm is used to improve the apparent resolution of, or quality of information extraction from, the eye.

In a 97th aspect, the assembly of any one of aspects 95-96, wherein the information fusion algorithm comprises an image super-resolution technique.

In a 98th aspect, the assembly of any one of aspects 95-97, wherein the information fusion algorithm is used to improve an image of an iris of the eye In a 99th aspect, the assembly of any one of aspects 95-98, wherein the information fusion algorithm comprises Iris-Code extraction (e.g., John Daugman, et al. 2006) and a subsequent fusion of resulting Iris-Codes to form a single estimate of the Iris-Code of the wearer.

In a 100th aspect, the assembly of any of aspects 86-99, wherein the assembly is configured for use of the image segments for improving eye pose estimation or tracking.

In a 101st aspect, the assembly of aspect 100, wherein the three dimensional reconstruction of the eye, iris, pupil, and cornea (or any subset of these) is used with the image segments directly for improving coverage of the eye in pose estimation.

In a 102nd aspect, the assembly of any one of aspects 86-101, wherein the reflective element comprises an OAVDOE including optical power to add or reduce beam divergence.

In a 103rd aspect, the assembly of any one of aspects 86-102, wherein the reflective element includes any number of segments (e.g., two, three, six, or nine segments).

In a 104th aspect, the assembly of any one of aspects 86-103, wherein the reflective element is configured to reflect infrared light and the viewing camera is sensitive to infrared light.

In a 105th aspect, the assembly of aspect 104, wherein the reflective element comprises a hot mirror configured to reflect in the infrared but otherwise transparent to visible light.

In a 106th aspect, the assembly of any one of aspects 86-105, further comprising an offset lens (e.g., as in tilt-shift photography) with a normal to the viewing camera parallel to a normal of the surface comprising the reflective element.

In a 107th aspect, a head mounted display (HMD) is disclosed. The HMD comprises a pair of displays, wherein each display comprises the imaging assembly of any one of aspects 86-106, and wherein one assembly of the pair is configured for each eye of the wearer.

CONCLUSION

Each of the processes, methods, and algorithms described herein and/or depicted in the attached figures may be embodied in, and fully or partially automated by, code modules executed by one or more physical computing systems, hardware computer processors, application-specific circuitry, and/or electronic hardware configured to execute specific and particular computer instructions. For example, computing systems can include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some implementations, particular operations and methods may be performed by circuitry that is specific to a given function.

Further, certain implementations of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities can be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto can be performed in other sequences that are appropriate, for example, in serial, in parallel, or in some other manner. Tasks or events may be added to or removed from the disclosed example embodiments. Moreover, the separation of various system components in the implementations described herein is for illustrative purposes and should not be understood as requiring such separation in all implementations. It should be understood that the described program components, methods, and systems can generally be integrated together in a single computer product or packaged into multiple computer products. Many implementation variations are possible.

The processes, methods, and systems may be implemented in a network (or distributed) computing environment. Network environments include enterprise-wide computer networks, intranets, local area networks (LAN), wide area networks (WAN), personal area networks (PAN), cloud computing networks, crowd-sourced computing networks, the Internet, and the World Wide Web. The network may be a wired or a wireless network or any other type of communication network.

The systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure. Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. No single feature or group of features is necessary or indispensable to each and every embodiment.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted can be incorporated in the example methods and processes that are schematically illustrated. For example, one or more additional operations can be performed before, after, simultaneously, or between any of the illustrated operations. Additionally, the operations may be rearranged or reordered in other implementations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A display system comprising:
   an optical element configured to display an image to a user, the optical element configured to be positioned forward an eye of the user;
   a forward-facing imager configured to be mounted rearward the eye of the user and configured to provide a depth of field, for imaging an eye region of the user, that is approximately twice as large as a backward-facing imager; and
   a reflective element disposed in or on the optical element, the reflective element configured to reflect toward the forward-facing imager infrared light received from the eye of the user.

2. The display system of claim 1, wherein the optical element comprises a light field display.

3. The display system of claim 1, wherein the reflective element comprises a hot mirror, an off-axis diffractive optical element (DOE), an off-axis holographic mirror (OAHM), or an off-axis volumetric diffractive optical element (OAVDOE).

4. The display system of claim 1, wherein the reflective element comprises a plurality of segments having different optical power or different reflection angle.

5. The display system of claim 4, wherein each of the plurality of segments is configured as a virtual camera imaging the eye at a correspondingly different angular location.

6. The display system of claim 5, wherein at least one of the plurality of segments is configured to generate the respective virtual camera at infinity.

7. The display system of claim 4, wherein to image the eye, the imager uses an upper segment when the user is looking upward and a lower segment when the user is looking downward.

8. The display system of claim 4, wherein to image the eye the display system selects a segment of the plurality of segments that has the least occlusion by eyelashes or eyelids of the user.

9. The display system of claim 1, further comprising:
   non-transitory memory configured to store images of the eye of the user obtained by the forward-facing imager; and
   a hardware processor in communication with the non-transitory memory, the hardware processor programmed to:
   access the images of the eye; and
   perform one or more of the following:
     track the eye of the user;
     extract biometric information associated with the eye of the user;
     reconstruct a shape of a portion of the eye of the user;
     estimate an accommodation state of the eye of the user; or
     image a retina, an iris, or other element of the eye of the user.

10. The display system of claim 9, wherein the hardware processor is programmed to estimate an accommodation state of the eye of the user.

11. The display system of claim 10, wherein to estimate the accommodation state of the eye of the user, the hardware processor is programmed to estimate distortion of an apparent location of the pupil of the eye of the user.

12. The display system of claim 9, wherein the hardware processor is programmed to reconstruct a shape of a portion of the eye of the user.

13. The display system of claim 12, wherein the hardware processor is programmed to utilize the shape of the portion of the eye of the user to estimate orientation of the eye.

14. The display system of claim 13, wherein to estimate orientation of the eye, the hardware processor is programmed to estimate location of a bulge of the cornea of the eye.

15. A head mounted display system comprising:
   a frame configured to support the display system according to claim 1 such that the optical element is positioned forward a first eye of the user.

16. The head mounted display system of claim 15, wherein the frame supports a second display system according to claim 1 such that the optical element of the second display system is positioned forward a second eye of the user.

* * * * *